US008574875B2

(12) United States Patent
    Scholten et al.

(10) Patent No.: US 8,574,875 B2
(45) Date of Patent: Nov. 5, 2013

(54) BACTERIAL STRAIN AND PROCESS FOR THE FERMENTATIVE PRODUCTION OF ORGANIC ACIDS

(75) Inventors: Edzard Scholten, Mannheim (DE); Dirk Dägele, Vogtsburg (DE); Stephan Haefner, Speyer (DE); Hartwig Schröder, Nußloch (DE)

(73) Assignee: BASF SE (DE)

( * ) Notice: Subject to any disclaimer, the term of this patent is extended or adjusted under 35 U.S.C. 154(b) by 464 days.

(21) Appl. No.: 12/673,714

(22) PCT Filed: Aug. 14, 2008

(86) PCT No.: PCT/EP2008/006714
    § 371 (c)(1),
    (2), (4) Date: Feb. 16, 2010

(87) PCT Pub. No.: WO2009/024294
    PCT Pub. Date: Feb. 26, 2009

(65) Prior Publication Data
    US 2011/0008851 A1    Jan. 13, 2011

(30) Foreign Application Priority Data
    Aug. 17, 2007 (EP) .................................. 07114574

(51) Int. Cl.
    *C12P 17/10* (2006.01)
(52) U.S. Cl.
    USPC ............ 435/121; 435/158; 435/145; 435/252
(58) Field of Classification Search
    None
    See application file for complete search history.

(56) References Cited

U.S. PATENT DOCUMENTS

| | | | |
|---|---|---|---|
| 4,550,185 A | 10/1985 | Mabry et al. | |
| 5,504,004 A | 4/1996 | Guettler et al. | |
| 5,573,931 A | 11/1996 | Guettler et al. | |
| 5,723,322 A | 3/1998 | Guettler et al. | |
| 6,596,521 B1 | 7/2003 | Chang et al. | |
| 7,063,968 B2 | 6/2006 | Lee et al. | |
| 7,192,761 B2 | 3/2007 | Zeikus et al. | |
| 7,256,016 B2 | 8/2007 | San et al. | |
| 7,262,046 B2 | 8/2007 | Ka-Yiu et al. | |
| 7,470,531 B2 | 12/2008 | Rehberger et al. | |
| 2007/0042481 A1 | 2/2007 | Lee et al. | |
| 2008/0293101 A1 | 11/2008 | Peters et al. | |
| 2009/0137825 A1 | 5/2009 | Bauduin et al. | |
| 2009/0155869 A1 | 6/2009 | Buelter et al. | |
| 2010/0044626 A1 | 2/2010 | Fischer et al. | |
| 2010/0159542 A1* | 6/2010 | Scholten et al. | 435/145 |
| 2010/0159543 A1* | 6/2010 | Scholten et al. | 435/145 |
| 2010/0324258 A1 | 12/2010 | Zelder et al. | |
| 2011/0300589 A1* | 12/2011 | Schroder et al. | 435/121 |

FOREIGN PATENT DOCUMENTS

| | | |
|---|---|---|
| EP | 0805208 A1 | 5/1997 |
| EP | 1842843 A1 | 10/2007 |
| EP | 2202294 A1 | 6/2010 |
| EP | 2204443 A1 | 7/2010 |
| JP | 2008011714 | 1/2008 |
| WO | WO-02/00846 A1 | 1/2002 |
| WO | WO-03/040690 A2 | 5/2003 |
| WO | WO-2005/052135 A1 | 6/2005 |
| WO | WO-2006/034156 A2 | 3/2006 |
| WO | WO-2006/066839 A2 | 6/2006 |
| WO | WO-2008/013405 A1 | 1/2008 |
| WO | WO-2009/024294 A1 | 2/2009 |

OTHER PUBLICATIONS

Guettler et al (Int'l J. of Systematic Bacter., 1999, vol. 49, pp. 207-216).*
Lee et al. (Applied and Environmental Microbiology, vol. 72, No. 3, Mar. 2006, pp. 1939-1948).*
Redfield et al. (BMC Evolutionary Biology, 2006, vol. 6 (82), pp. 1-15).*
Lee et al. (Appl. Microbiol. Biotechnol., 2002, vol. 58, pp. 663-668).*
Vlysidis et al. ( AIChE100 2008 Annual Meeting).*
Zeikus (Appl. Microbiol Biotech., 1999, vol. 51, pp. 545-552).*
Database Em-Pro *Mannheimia succiniproducens* MBEL55E Sep. 18, 2004, XP002498827 accession No. AE016827 nt 1495543-151059 nt 2233952-2235468 99.7% identity with Seq ID 1 abstract.
Dharmadi Y, et al., "Anaerobic Fermentation of Glycerol by *Escherichia coli*: A New Platform for Metabolic Engineering," Biotechnology and Bioengineering, vol. 94, No. 5, pp. 821-829 (2006).
Hong S.H. et al., "The genome sequence of the capnophilic rumen bacterium *Mannheimia succiniciproducens*" Nature Biotechnology, vol. 22, No. 10, (Oct. 2004), pp. 1275-1281, XP002498825 ISSN: 1087-0156 table 1.
Janssen P.H., "Characterization of a succinate-fermenting anaerobic bacterium isolated from a glycolate-degrading mixed culture," Arch Microbiol (1991)155: pp. 288-293.
Lee J., "Biological conversion of lignocellulosic biomass to ethanol," Journal of Biotechnology 56: (1997) pp. 1-24.
Lee P.C., et al., "Isolation and characterization of a new succinic acid-producing bacterium, *Mannheimia succiniciproducens* MBEL55E, from bovine rumen," Appl Microbiol Biotechnol (2002a) 58: pp. 663-668.
Lee P.C., et al., Succinic Acid Production with Reduced By-Product Formation in the Fermentation of *Anaerobiospirillum succiniciproducens* Using Glycerol as a Carbon Source, Biotechnology and Bioengineering, vol. 72, No. 1, pp. 41-48 (2001).
Maidak B.L., et al., "A new version of the RDP (Ribosomal Database Project),". Nucleic Acids Research, 1999, vol. 27, No. 1, pp. 171-173.
McKinlay J, Zeikus J, Vieille C (2005) Insights into *Actinobacillus succinogenes* fermentative metabolism in a chemically defined growth medium. Appl Environ Microbiol 71: 6651-6656.

(Continued)

*Primary Examiner* — Hope Robinson
(74) *Attorney, Agent, or Firm* — Roberte M. D. Makowski

(57) ABSTRACT

The present invention relates to a novel bacterial strain designated DD1, which has the ability to produce organic acids, in particular succinic acid (SA), which was originally isolated from bovine rumen, and is capable of utilizing glycerol as a carbon source; and variant strains derived there from retaining said capability; as well as to methods of producing organic acids, in particular succinic acid by making use of said microorganism.

16 Claims, 9 Drawing Sheets

(56) References Cited

OTHER PUBLICATIONS

Nili N., et al., "A defined medium for rumen bacteria and identification of strains impaired in de *novo* biosynthesis of certain amino acids," Letters in Applied Microbiology 1995, 21d pp. 69-74.

Peters-Wendisch, P.G. et al.,$C_3$-Carboxylation as an anaplerotic reaction in phosphoenolpyruvate carboxylase-deficient *Corynebacterium glutamicum*, Arch Microbiol (1996) 165: pp. 387-396.

Rainey F.A., et al., "The genus *Nocardiopsis* Represents a Phylogenetically Coherent Taxon and a Distinct Actinomycete Lineage: Proposal of *Nocardlopsaceae* fam. nov.," International Journal of Systematic Bacteriology, vol. 46, No. 4, 1996, pp. 1088-1092.

Saitou N., et al., "The Neighbor-joining Method: A New Method for Reconstructing Phylogenetic Trees,". Mol. Biol. Evol. 4(4): pp. 406-425 (1987).

Schoelten E., et al., "Succinic acid production by a newly isolated bacterium" Biotechnol. Lett., Jul. 24, 2008, XP002498826 [retrieved on Aug. 7, 2008] DOI 10.1007/s10529-008-9806-2.

Song H., et al., "Production of succinic acid by bacterial fermentation," Enzyme and Microbial Technology 39: (2006) pp. 352-361.

Song H., et al., "Development of chemically defined medium for *Mannheimia succiniciproducens* based on its genome sequence," Appl Microbiol Biotechnol (2008) 79: pp. 263-272.

Yazdani S, et al., "Anaerobic fermentation of glycerol: a path to economic viability for the biofuels industry," Current Opinion Biotechnology 2007,18: pp. 213-219.

"SubName: Full-Isocitrate lyase", EMBL database, Accession No. A1JRX1, Feb. 6, 2007.

"RecName: Full-Malate synthase" EMBL database, Accession No. A1JRX8, Feb. 6, 2007.

"pflD PflD protein [*Mannheimia succiniciproducens* MBEL55E]", Database NCBI, Accession No. 3075405, Dec. 18, 2010.

"IdhA D-lactate dehydrogenase [*Mannheimia succiniciproducens* MBEL55E (strain; MBEL55E", Database NCBI, Accession No. 3075603, May 21, 2011.

"pflA pyruvate formate lyase-activating enzyme 1 [*Shigella boydii* CDC 3083-94]", Database NCBI, Accession No. 6268899, Jan. 14, 2011.

"ybiW predicted pyruvate formate lyase [*Escherichia coli* str. K-12 substr. MG1655]", Database NCBI, Accession No. 945444, Feb. 28, 2011.

"pflB pyruvate formate lyase I [*Escherichia coli* str. K-12 substr. MG1655]", Database NCBI, Accession No. 945514, Feb. 28, 2011.

"IdhA fermentative D-lactate dehydrogenase, NAD-dependent [*Escherichia coli* str. K-12 substr. MG1655]" Database NCBI, Accession No. 946315, May 21, 2011.

"tdcE pyruvate formate-lyase 4/2-ketobutyrate formate-lyase [*Escherichia coli* str. K-12 substr. MG1655]", Database NCBI, Accession No. 947623, Feb. 28, 2011.

"pflD predicted formate acetyltransferase 2 (pyruvate formate lyase II) [*Escherichia coli* str. K-12 substr. MG1655]", Database NCBI Accession No. 948454, Feb. 28, 2011.

"pyruvate formate lyase-activating enzyme 1 [*Shigella boydii* CDC 3083-94]", Database NCBI, Accession No. YP_001880903.1, Jan. 5, 2011.

"Formate acetyltransferase 1", Database UniProtKB, Accession No. P09373, Feb. 8, 2011.

"Formate acetyltransferase 2", Database UniProtKB, Accession No. P32674, Feb. 8, 2011.

"Keto-acid formate acetyltransferase", Database UniProtKB, Accession No. P42632, Feb. 8, 2011.

"Putative formate acetyltransferase", Database UniProtKB, Accession No. P75793, Feb. 8, 2011.

"PflD protein", Database UniProtKB, Accession No. Q65VK2, Nov. 30, 2010.

Berrios-Rivera, S., et al., "The Effect of Increasing NADH Availability on the Redistribution of Metabolic Fluxes in *Escherichia coli* Chemostat Cultures", Metabolic Engineering, vol. 4, No. 3, (2002), pp. 230-237.

Broun, P., et al., "Catalytic Plasticity of Fatty Acid Modification Enzymes Underlying Chemical Diversity of Plant Lipids", Science, 1998, vol. 282, pp. 1315-1317.

Chica, R.A., et al., "Semi-rational approaches to engineering enzyme activity: combining the benefits of directed evolution and rational design", Current Opinion Biotechnology, 2005, vol. 16, pp. 378-384.

Devos, D., et al., "Practical Limits of Function Prediction", PROTEINS: Structure, Function and Genetics, 2000, vol. 41, pp. 98-107.

Dousse, F., et al., "Routine phenotypic identification of bacterial species of the family *Pasteurellaceae* isolated from animals," J. Vet. Diagn. Invest., 2008, vol. 20, pp. 716-724.

Durchschlag, H., et al., "Large-Scale Purification and Some Properties of Malate Synthase from Baker's Yeast", Eur. J. biochem., vol. 114, (1981), pp. 114-255.

Eggerer, H., et al., "Über das Katalyseprinzip der Malat-Synthase", European J. Biochem., vol. 1, (1967), pp. 447-475.

European Search Report EP 09 17 8050 dated Feb. 23, 2010.

Feng, D.-F., et al., "Progressive Sequence Alignment as a Prerequisite to Correct Phylogenetic Trees", J. Mol. Evol., vol. 25, (1987), pp. 351-360.

Ferry, J. G., "Formate Dehydrogenase", FEMS Microbiology Reviews, vol. 87, (1990), pp. 377-382.

Frey, J., "Construction of a Broad Host Range Shuttle Vector for Gene Cloning and Expression in *Actinobacillus pleuropneumoniae* and Other *Pasteurellaceae*", Res. Microbial, vol. 143, (1992), pp. 263-269.

Guo, H.H., et al., "Protein tolerance to random amino acid change", PNAS, 2004, vol. 101, No. 25, pp. 9205-9210.

Higgins, D. G., et al., "Fast and Sensitive Multiple Sequence Alignments on a Microcomputer", vol. 5, No. 2, (1989), pp. 151-163.

Hoyt, J. C., et al., "*Escherichia coli* Isocitrate Lyase: Properties and Comparisons", Biochimica et Biophysica Acta, vol. 966, (1988), pp. 30-35.

Hong, S. H., et al., "Metabolic Flux Analysis for Succinic Acid Production by Recombinant *Escherichia coli* with Amplified Malic Enzyme Activity," Biotechnology and Bioengineering, 2001, vol. 74, No. 2, pp. 89-96.

Kim, J. M., et al., "Development of a Markerless Gene Knock-Out System for *Mannheimia succiniciproducens* Using a Temperature-Sensitive Plasmid", FEMS Microbiol Lett, vol. 278, (2008), pp. 78-85.

Kimchi-Sarfaty, C., et al. "A 'silent' polymorphism in the MDR1 gene changes substrate specificity", Science, 2007, vol. 315, pp. 525-528.

Kisselev, L., et al., "Polypeptide release factors in prokaryotes and eukaryotes: same function, different structure", Structure, 2002, vol. 10, pp. 8-9.

Kuhnert, P., et al., "*Pasteurellaceae*, Biology, Genomics, and Molecular Aspects", (2008), ISBN 978-1-904455-34-9.

Knappe, J., et al., "A radical-chemical route to acetyl-CoA: the anaerobically induced pyruvate formate-lyase system of *Escherichia coli*," FEMS Microbiology Reviews, 1990, vol. 75, pp. 383-398.

Knappe, J., et al., "Pyruvate formate-lyase mechanism involving the protein-based glycyl radical," Biochemical Society Transactions, 1993, vol. 21, pp. 731-734.

Lee, S. Y., et al., "From Genome Sequence to Integrated Bioprocess for Succinic Acid Production by *Mannheimia succiniciproducens*", Applied Microbiology Biotechnology, vol. 79, No. 1, (2008), pp. 11-22.

Lee, S. Y., "BTEC 18Genome-Scale Metabolic engineering of *Mannheimia succiniciproducens* for Enhanced Succinic Acid Production", Genomic and Systems Approaches to Metabolic Engineering, The 229th ACS National Meeting in San Diego, CA., Mar. 13-17, 2005.

Leenhouts, K. J., et al., "Campbell-Like Integration of Heterologous Plasmid DNA into the Chromosome of *Lactococcus lactis* subsp. *lactis*", Applied and Environmental Microbiology, vol. 55, (1989), pp. 394-400.

Lin, H., et al., "Effect of *Sorghum vulgare* phosphoenolpyruvate carboxylase and *Lactococcus lactis* pyruvate carboxylase coexpression on succinate production in mutant strains of *Escherichia coli*," Appl. Microbiol. Biotechnol., 2005, vol. 67, pp. 515-523.

(56) References Cited

OTHER PUBLICATIONS

Mackintosh, C., et al., "Purification and Regulatory Properties of Isocitrate Lyase From *Escherichia coli* ML308", Biochem. J., vol. 250, (1988), pp. 25-31.

Müller, U., et al., "Formate Dehydrogenase from *Pseudomonas oxalaticus*", Eur. J. Biochem, vol. 83, (1978), pp. 485-498.

Nackley, A.G., et al. "Human catechol-o-methyltransferase haplotypes modulate protein expression by altering rRNA secondary structure", Science, 2006, vol. 314, pp. 1930-1933.

Needleman, S. B., et al., "A General Method Applicable to the Search for Similarities in the Amino Acid Sequence of Two Proteins", J. Mol. Biol., vol. 48, (1970), pp. 443-453.

Pascal, M. C., et al., "Mutants of *Escherichia coli* K 12 with Defects in Anaerobic Pyruvate Metabolism," J. Gen. Microbiol., 1981, vol. 124, pp. 35-42.

Robertson, E. F., et al., "Purification and Characterization of Isocitrate Lyase from *Escherichia coli*", Current Microbiology, vol. 14, (1987), pp. 347-350.

Sanchez, A. M., et al., "Novel pathway engineering design of the anaerobic central metabolic pathway in *Escherichia coli* to increase succinate yield and productivity," Metabolic Engineering, 2005, vol. 7, pp. 229-239.

Sauna, Z.E., et al., "Silent polymorphisms speak: How they affect pharmacogenomics and the treatment of cancer", Cancer Research, 2007, vol. 67, No. 2, pp. 9609-9612.

Scholten, E., et al., "Continuous Cultivation Approach for Fermentative Succinic Acid Production from Crude Glycerol by *Basfia succiniciproducens* DD1", Biotechnol Lett, vol. 31, (2009), pp. 1947-1951.

Seffernick, J.L., et al. "Melamine deaminase and atrazine chlorohydrolase; 98 percent identical but functionally different", J. Bacteriology, 2001, vol. 183, No. 8, pp. 2405-2410.

Sen, S., et al, "Developments in directed evolution for improving enzyme functions", Appl. Biochem. Biotechnol., 2007, vol. 143, pp. 212-223.

Smith, T.F., et al., "Identification of Common Molecular Subsequences," *J. Mol. Biol.* (1981), vol. 147, pp. 195-197.

Sundaram, T. K., et al, "Monomeric Malate Synthase from a Thermophilic *Bacillus*", Archives of Biochemistry and Biophysics, vol. 199, No. 2, (1980), pp. 515-525.

Thomson, N. R, et al. "The complete genome sequence and comparative genome analysis of the high pathogenicity *Yersinia enterocolitica* strain 8081", PLoS Genetics, 2006, vol. 2, No. 12, pp. 2039-2051.

Tishkov, V.I, et al., "Catalytic Mechanism and Application of Formate Dehydrogenase", Biochemistry (Moscow), vol. 69, No. 11, (2004), pp. 1252-1267.

Varenne, S., et al., "A Mutant of *Escherichia coli* Deficient in Pyruvate Formate Lyase," Molec. Gen. Genet., 1975, vol. 141, pp. 181-184.

Watanabe, S., et al., "Purification and Characterization of a Cold-Adapted Isocitrate Lyase and a Malate Synthase from *Colwellia maris*, a Psychrophilic Bacterium", Biosci. Biotechnol. Biochem., vol. 65, No. 5, (2001), pp. 1095-1103.

Whisstock, J.C.,et al. "Prediction of protein function from protein sequence", Q. Rev. Biophysics, 2003, vol. 36, No. 3, pp. 307-340.

White, W. T., et al., "Species and size compositions and reproductive biology of rays (*Chondrichthyes, Batoidea*) caught in target and non-target fisheries in eastern Indonesia," J. Fish Biol., 2007, vol. 70, pp. 1809-1837.

Wishart, M.J., et al. "A single mutation converts a novel phosphotyrosine binding domain into a dual-specificity phosphatase", J. Biol. Chem., 1995, vol. 270, No. 45, pp. 26782-26785.

Witkowski, A. et al., Conversion of b-ketoacyl synthase to a malonyl decarboxylase by replacement of the active cysteine with glutamine. Biochemistry, 1999, vol. 38, pp. 11643-11650.

Zhang, X., et al., "Fermentation of Glycerol to Succinate by Metabolically Engineered Strains of *Escherichia coli*," Applied and Environmental Microbiology, 2010, vol. 76, No. 8, pp. 2397-2401.

Zhu, J., et al., "Effect of a single-gene knockout on the metabolic regulation in *Escherichia coli* for D-lactate production under microaerobic condition," Metab. Engineering, 2005, vol. 7, pp. 104-115.

International Preliminary Report on Patentability, PCT/EP2010/051798, issued May 12, 2011.

International Preliminary Report on Patentability, PCT/EP2008/006714, issued Feb. 24, 2010.

European Opinion EP 09 17 8050 dated Feb. 23, 2010.

European Search Report EP 09 17 8048 dated Mar. 31, 2010.

Patentability Opinion of EP Searching Authority—EP 09 178 048.6, mailed Apr. 13, 2010.

* cited by examiner

```
   1 tttgatcctg gctcagattg aacgctggcg gcaggcttaa cacatgcaag tcgaacggta
  61 gcgggaggaa agcttgcttt ctttgccgac gagtggcgga cgggtgagta atgcttgggg
 121 atctggctta tggaggggga taacgacggg aaactgtcgc taataccgcg taatatcttc
 181 ggattaaagg gtgggacttt cgggccaccc gccataagat gagcccaagt gggattaggt
 241 agttggtggg gtaaaggcct accaagccga cgatctctag ctggtctgag aggatgacca
 301 gccacactgg aactgagaca cggtccagac tcctacggga ggcagcagtg gggaatattg
 361 cacaatgggg gaaacctga tgcagccatg ccgcgtgaat gaagaaggcc ttcgggttgt
 421 aaagttcttt cggtgacgag gaaggtgttt gttttaatag gacaagcaat tgacgttaat
 481 cacagaagaa gcaccggcta actccgtgcc agcagccgcg gtaatacgga gggtgcgagc
 541 gttaatcgga ataactgggc gtaaagggca tgcaggcgga cttttaagtg agatgtgaaa
 601 gccccgggct taacctggga attgcatttc agactgggag tctagagtac ttagggagg
 661 ggtagaattc cacgtgtagc ggtgaaatgc gtagagatgt ggaggaatac cgaaggcgaa
 721 ggcagcccct tgggaagata ctgacgctca tatgcgaaag cgtgggagc aaacaggatt
 781 agataccctg gtagtccacg ccgtaaacgc tgtcgatttg gggattgggc tttaggcctg
 841 gtgctcgtag ctaacgtgat aaatcgaccg cctggggagt acggccgcaa ggttaaaact
 901 caaatgaatt gacggggggcc cgcacaagcg gtggagcatg tggtttaatt cgatgcaacg
 961 cgaagaacct taccactct tgcatccag agaatcctgt agagatacgg gagtgccttc
1021 gggagctctg agacaggtgc tgcatggctg tcgtcagctc gtgttgtgaa atgttgggtt
1081 aagtcccgca acgagcgcaa cccttatcct ttgttgccag catgtaaaga tgggaactca
1141 aaggagactg ccggtgacaa acggaggaa ggtgggatg acgtcaagtc atcatggccc
1201 ttacgagtag gctacacac gtgctacaat ggtgcataca gagggcggc ataccgcgag
1261 gtagagcgaa tctcagaaag tgcatcgtag tccggattgg agtctgcaac tcgactccat
1321 gaagtcggaa tcgctagtaa tcgcaaatca gaatgttgcg gtgaatacgt tcccgggcct
1381 tgtacacacc gcccgtcaca ccatgggagt gggttgtacc agaagtagat agcttaacct
1441 tcgggggggg cgtttaccac ggtatgattc atgactgggg tgaagtcgta acaaggtaac
1501 cgtagggaa cctgcgg
```

Fig.2

```
agtaataacg aacgacacag gtataagaat acttgaggtt gtatggttaa gtgactaagc    60
gtacaaggtg gatgccttgg caatcagagg cgaagaagga cgtgctaatc tgcgaaaagc   120
ttgggtgagt tgataagaag cgtctaaccc aagatatccg aacgggcaa cccagtagat   180
gaagaatcta ctatcaataa ccgaatccat aggttattga ggcaaaccgg gagaactgaa   240
acatctaagt accccgaggs aagaaatca accgagatta cgtcagtagc ggcgagcgaa   300
agcgtaagag ccggcaagtg atagcatgag gattagagga atcggctggg aagccggcg   360
gcacagggtg atagcccgt acttgaaaat cattgtgtgg tactgagctt gcgagaagta   420
gggcgggaca cgagaaatcc tgtttgaaga aggggggacc atcctccaag gctaaatact   480
cctgattgac cgatagtgaa ccagtactgt gaaggaaagg cgaaaagaac ccggtgagg   540
ggagtgaaat agaacctgaa accttgtacg tacaagcagt gggagcccgc gagggtgact   600
ggtaccttt tgtataatgg gtcagcgact tatattatgt agcgaggtta accgaatagg   660
ggagccgaag ggaaaccgag tcttaactgg gcgtcgagtt gcatgatata gacccgaaac   720
ccggtgatct agccatgggc aggttgaagg ttgggtaaca ctaactgagg gaccgaaccg   780
actaatgttg aaaactagc ggatgacctg tggctggggg tgaaaggcca atcaaacgg   840
gagatagctg gttctcccg aaatctattt aggtagagcc ttatgtgaat accttcgggg   900
gtagagcact gttcggcta ggggccatc cggcttacc aaccgatgc aaactgcgaa   960
tacgaagag taatgcatag gagacacacg gcgggtgcta acgttcgtcg tggagaggga  1020
aacaaccag accgccagct aaggtccaa agtttatatt aagtgggaaa cgaagtggga  1080
aggcttagac agctaggatg ttggcttaga agcagccatc atttaaagaa agcgtaatag  1140
ctcactagtc gagtcggct gcgggaaga tgtaacgggg ctcaaatata gcaccgaagc  1200
tgcggcatca ggcgtaagcc tgttgggtag gggagcgtcg tgtaagcgga agaaggtggt  1260
tcgagagggg tgctcgacgt atcacgagtc cgaatgctga cataagtaac gataaacgg  1320
gtgaaasacc cgttcgccgg aagaccaagg gttcctgtcc aacgttaatc ggggcagggt  1380
gagtcggccc ctaaggcgag gctgaagagc gtagtcgatg ggaacgggt taatattccc  1440
gtacttgtta tacttgcgat gtggggacgg agtaggttag gttatcgacc tgttggaaaa  1500
ggtcgttaa gttggtaggt ggagcgttta ggcaaatccg gacgcttatc aacaccgaga  1560
gatgatgacg aggcgctaag gtgccgaagt aaccgatacc acattccag gaaaagccac  1620
taagcgtcag attataataa acgtactat aaacgacac aggtggtcag gtagagaata  1680
ctcaggcgct tgagagaact cggtgaagg aactaggcaa aatagcacg taacttcggg  1740
agaaggtgcg ccggcgtaga ttgtagaggt ataccttga aggttgaacc gtcgaagtg  1800
acccgctggc tgcaactgtt tattaaaaac acagcactct gcaaacacga aagtggacgt  1860
atagggtgtg atgcctgccc ggtgctggaa ggttaactga tggcgttatc gcaagagaag  1920
cgcctgatcg aagcccgagt aaacggcggc cgtaactata acggtcctaa ggtacgaggaa 1980
tccttgtcg ggtaagttcc gacctgcaag aattgcataa tgatgccag gcgtctcca  2040
ccgagactc agtgaaattg aaatcgccgt gaagatgcgg tgtaccgcag gctagacgga  2100
aagacccgt gaaccttac tatagcttga cactgaacct tgaatttga tgtgtaggat  2160
aggtgggagg ctttgaagcg gtaacgccag ttatcgtgga gccatcctg aaataccacc  2220
ctttaacgtt tgatgttcta acgaagtgcc cggaacgggt actcggacag tgtctggtgg  2280
gtagttgac tggggcggtc tcctccaaa gagtaacgga ggagcacgaa ggtttgctaa  2340
tgacggtcgg gagtggacgc atcactggtg ttccggttgt ctcgccagac gcattgcgag  2400
caagtcgagc aggtgcgaaa gcaggtcata gtgatccggt ggttctgaat ggaaggcca  2460
tcgctcaacg gataaaaggt actccgggga taacaggctg ataccccaa agagttcata  2520
tcgacggcgg tgtttggcac ctcgatgtcg gctcatcaca tcctgggct gaagtaggtc  2580
ccaagggtat ggctgttcgc catttaaagt ggtacgcgag ctggtttcaa acgtcgtga  2640
gacagtttgg tccctatctg ccgtgggcgt tggagaattg agaggggctg ctcctagtac  2700
gagaggaccg gagtggacgc atcactggtg ttccggttgt ctcgccagac gcattgcgag  2760
gtagctacat ggggaagaga taagtgctga aagcatctaa gcagaaact tgcctgaga  2820
tgagttctcc cagtatttaa tactgtaagg gttgttggag acgacgcgt agataggcg  2880
ggtgtaag cgttgcgaga cgttagcta accgtacta attgccgag aggttagcc  2940
atacaacgct caagtgtttt tggtagtgaa agttattacg gaataagtaa gtagtcaggg  3000
aatcggct                                                           3008
```

Fig.3

BACTERIAL STRAIN AND PROCESS FOR THE FERMENTATIVE PRODUCTION OF ORGANIC ACIDS

CROSS REFERENCE TO RELATED APPLICATIONS

This application is a National Phase filing under 35 U.S.C. §371 of PCT/EP2008/006714 filed Aug. 14, 2008, which claims priority to Patent Application No. 07114574.2, filed in Europe on Aug. 17, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing_60072. The size of the text file is 32 KB, and the text file was created on Jan. 23, 2013.

The present invention relates to a novel bacterial strain designated DD1, which has the ability to produce organic acids, in particular succinic acid (SA), which was originally isolated from bovine rumen, and is capable of utilizing glycerol as a carbon source; and variant strains derived there from retaining said capability; as well as to methods of producing organic acids, in particular succinic acid by making use of said microorganism.

BACKGROUND ART

The fermentative production of succinic acid (SA) from biomass has already drawn much attention because said acid represents an important constituent of synthetic resins or is a source of further valuable low-molecular chemical compounds, in particular tetrahydrofuran (THF), 1,4-butanediol (BDO), gamma-butyrolactone (GBL) and pyrrolidones (WO-A-2006/066839).

A SA-producing bacterium isolated from bovine rumen was described by Lee et al (2002a). The bacterium is a non-motile, non-spore-forming, mesophilic and capnophilic gram-negative rod or coccobacillus. Phylogenetic analysis based on the 16S rRNA sequence and physiological analysis indicated that the strain belongs to genus *Mannheimia* as a novel species, and has been named *Mannheimia succinicipro-ducens* MBEL55E. Under 100% $CO_2$ conditions, it grows well in the pH range of 6.0-7.5 and produces succinic acid, acetic acid and formic acid at a constant ratio of 2:1:1. When *M. succiniciproducens* MBEL55E was cultured anaerobically under $CO_2$-saturation with glucose as carbon source, 19.8 g/L of glucose were consumed and 13.3 g/L of SA were produced in 7.5 h of incubation.

A significant drawback of said organism is, however, its inability to metabolize glycerol, which, as a constituent of triacyl glycerols (TAGS), becomes readily available e.g. as by-product in the transesterification reaction of Biodiesel production (Dharmadi et al., 2006).

The fermentative production of succinic acid from glycerol has been described in the scientific literature (Lee et al., 2001; Dharmadi et al., 2006) and with glycerol higher yields [mass of SA produced/mass of raw material consumed] than with common sugars like glucose were achieved (Lee et al., 2001). However, the space time yield obtained with glycerol was substantially lower than with glucose (0.14 vs. 1.0 g SA/[L h]) and no crude glycerol was used.

Only in a few cases anaerobic metabolisation of glycerol to fermentation products have been described. *E. coli* is able to ferment glycerol under very specific conditions such as acidic pH, avoiding accumulation of the fermentation gas hydrogen, and appropriate medium composition. (Dharmadi et al 2006, Yazdani and Gonzalez 2007) Many microorganisms are able to metabolize glycerol in the presence of external electron acceptors (respiratory metabolism), few are able to do so fermentatively (i.e. in the absence of electron acceptors). The fermentative metabolism of glycerol has been studied in great detail in several species of the Enterobacteriaceae family, such as *Citrobacter freundii* and *Klebsiella pneumoniae*. Dissimilation of glycerol in these organisms is strictly linked to their capacity to synthesize the highly reduced product 1,3-propanediol (1,3-PDO) (Dharmadi et al 2006). The conversion of glycerol into succinic acid using *Anaerobiospirillum succiniciproducens* has been reported (Lee et al. 2001). This study demonstrated that succinic acid could be produced with little formation of by-product acetic acid by using glycerol as a carbon source, thus facilitating purification of succinic acid. The highest yield was obtained by intermittently feeding glycerol and yeast extract, a strategy that resulted in the production of about 19 g/L of succinic acid. It was noted, however, that unidentified nutritional components present in yeast extract were needed for glycerol fermentation to take place.

Carboxylation reactions of oxaloacetate catalyzed by the enzymes phopshoenolpyruvate carboxylase (PEPC), phopshoenolpyruvate carboxykinase (PEPCK) and pyruvate carboxylase (PycA) are utilizing $HCO_3^-$ as a source of $CO_2$ (Peters-Wendisch, P G et al). Therefore hydrogencarbonate sources such as $NaHCO_3$, $KHCO_3$, $NH_4HCO_3$ and so on can be applied to fermentation and cultivation media to improve the availability of $HCO_3^-$ in the metabolisations of substrates to succinic acid. The production of succinic acid from glucose has not been found to be dependent on the addition of $HCO_3^-$ in the prior art so far.

Biomass production by anaerobic organisms is limited by the amount of ATP produced from fermentative pathways. Biomass yield of glycerol in anaerobic organisms is lower than of saccharides, like hexoses such as glucose, fructose, pentoses such as xylose arabinose or disaccharides such as sucrose or maltose (Lee et al. 2001, Dharmadi 2007).

Saccharides, however, theoretically can be converted to succinic acid with a significantly lower yield than glycerol due to the lower reduction state of saccharides compared to the polyol glycerol. The combination of saccharides with glycerol have been found to function in an succinic acid producing anaerobic organisms (Lee et al. 2001), however without reaching succinic acid titers beyond 28 g/l.

There is, therefore, a need for further bacterial strains, which have the ability to produce organic acids, in particular SA, from glycerol. In particular, such strains should produce said acids with high productivity from glycerol, especially if crude glycerol e.g. from bio diesel production can be used without prior purification.

SUMMARY OF THE INVENTION

It is an object of the present invention to provide a bacterial strain having the ability to produce succinic acid from glycerol, especially crude glycerol.

Said object was solved by the present inventors who surprisingly isolated a novel bacterial strain, designated DD1, having the desired metabolic characteristic.

BRIEF DESCRIPTION OF THE FIGURES

FIG. 2 shows the 16S rDNA sequence (SEQ ID NO:1) of DD1

FIG. 3 shows the 23S rDNA sequence (SEQ ID NO:2) of DD1; its alignment to the corresponding six individual sequences of "*M. succiniciproducens*" MBEL55E; where differences between the DD1 sequence (bottom) and the MBEL55E sequences are highlighted is shown in the separate Annex 1;

Figure 1:
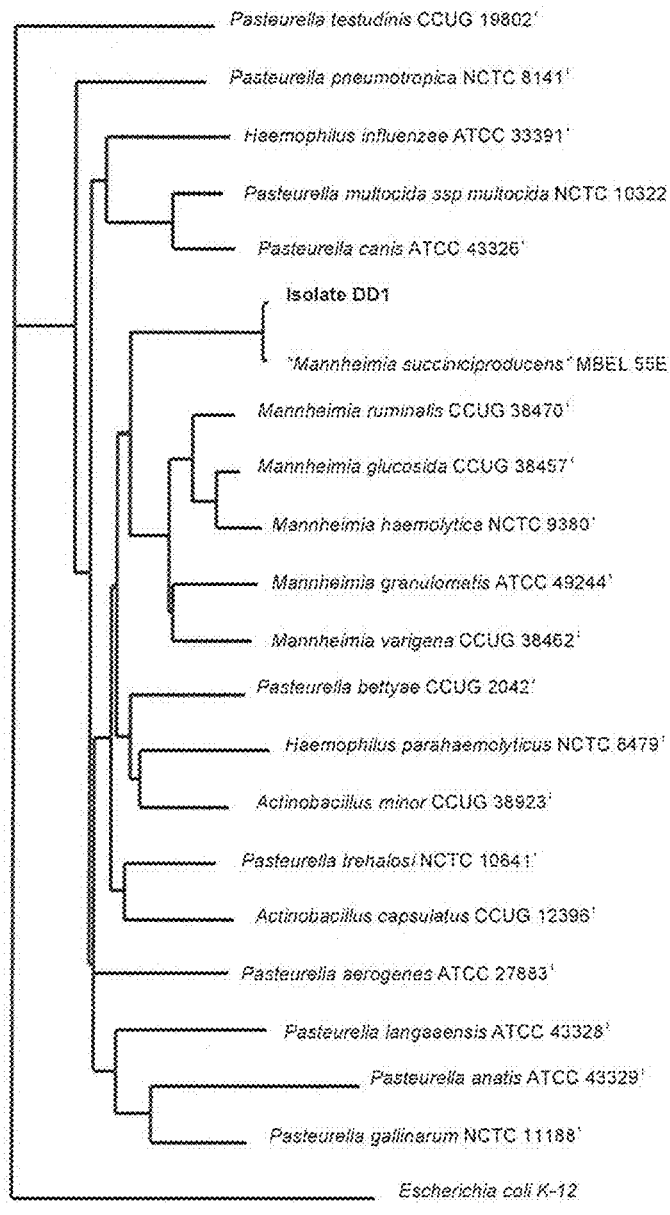
FIG. 1 shows the phylogenetic tree for DD1

Annex 1 shows an alignment of the 23S rDNA sequence (23s_rRNA_seq_rev, SEQ ID NO:2) of DD1 with the corresponding six individual sequences of "*M. succiniciproducens*" MBEL55E: 23s_rRNA_5 (SEQ ID NO: 7), 23s_rRNA_3 (SEQ ID NO: 5), 23s_rRNA_1 (SEQ ID NO: 3), 23s_rRNA_2 (SEQ ID NO: 4), 23s_rRNA_6 (SEQ ID NO: 8), 23s_rRNA_4 (SEQ ID NO: 6), where differences between the DD1 sequence (bottom) and the MBEL55E sequences are highlighted.

DETAILED DESCRIPTION OF THE INVENTION

A first embodiment of the invention relates to a bacterial strain, designated DD1, which may be isolated from bovine rumen, and is capable of utilizing glycerol (including crude glycerol) as a carbon source; and variant strains derived there from retaining said capability.

Preferably said strain has the ability to produce succinic acid from glycerol (including crude glycerol), in particular, under anaerobic conditions.

In particular, the novel strain has a 16S rDNA of SEQ ID NO:1 or a sequence which shows a sequence homology of at least 96, 97, 98, 99 or 99.9% and/or a 23S rDNA of SEQ ID NO:2 or a sequence which shows a sequence homology of at least 95, 96, 97, 98, 99 or 99.9%.

"Identity" or "homology" between two nucleotide sequences means identity of the residues over the complete length of the aligned sequences, such as, for example, the identity calculated (for rather similar sequences) with the aid of the program needle from the bioinformatics software package EMBOSS (Version 5.0.0, see webpage at emboss.sourceforge.net/what/) with the default parameters which are:
gapopen (penalty to open a gap): 10.0
gapextend (penalty to extend a gap): 0.5
datafile (scoring matrix file included in package): EDNAFUL An alignment of the 23S rDNA sequence of Strain DD1 to the corresponding six individual sequences of "*M. succiniciproducens*" MBEL55E is shown in Annex 1. Therein, the differences between the DD1 sequence (bottom) and the six 23S rDNA sequences of MBEL55E sequences are highlighted. The DD1 sequence (see also SEQ ID NO:2) represents the sequence information as obtained by sequencing the PCR amplified 23S rDNA of DD1. Sequencing experiments resulted in an unambiguous sequence information indicating that the 23S rDNA information derivable from DD1 may be used as distinguishing feature of the DD1 strain. Said DD1 sequence differs in at least 6 sequence positions from each individual MBEL55E sequence. The most significant difference is an insert of about 133 bp into each of the MBEL55E sequences (near position 1325), which is missing in the DD1 sequence. Further significant, specific sequence differences are at positions 451, 1741, 2040, 2041, 2045 and 2492 (numbering as used in the alignment).

The strain of the present invention also preferably shows at least one of the following additional metabolic characteristics:

a) production of succinic acid from sucrose; in particular, under anaerobic conditions;

b) production of succinic acid from maltose; in particular, under anaerobic conditions;

c) production of succinic acid from D-fructose; in particular, under anaerobic conditions;

d) production of succinic acid from D-galactose; in particular, under anaerobic conditions;

e) production of succinic acid from D-mannose; in particular, under anaerobic conditions;

f) production of succinic acid from D-glucose; in particular, under anaerobic conditions;

g) production of succinic acid from D-xylose; in particular, under anaerobic conditions;

h) production of succinic acid from L-arabinose; in particular, under anaerobic conditions;

i) no utilization of xylitol, inositol and sorbitol;

j) growth both under aerobic and anaerobic conditions;

k) growth at initial glucose concentrations of 75 g/L or more;

l) ammonia tolerance.

In particular, said strain shows at least 1, 2, 3, 4, 5, 6, 7, 8, 9, 10, 11 or all of said additional features.

DD1 was, for example, further analyzed for the capability to co-metabolize a saccharide and the polyol glycerol. It was found that DD1 is capable to co-metabolize maltose and glycerol resulting in biomass formation, succinic acid formation and simultaneous maltose and glycerol utilisation.

The term "acid" (in the context of organic mono or dicarboxylic acids as referred to herein, i.p. acetic, lactic and succinic acid) has to be understood in its broadest sense and also encompasses salts thereof, as for example alkali metal salts, like Na and K salts, or earth alkali salts, like Mg and Ca salts, or ammonium salts; or anhydrides of said acids.

The term "crude glycerol" has to be understood as untreated glycerol-containing stream as it accrues in processes in which glycerol is a by product, as for example the production of bio diesel or bio ethanol. Unless otherwise stated the term "glycerol" as used herein also encompasses "crude glycerol".

In a preferred embodiment the invention relates to a bacterial strain DD1 as deposited with DSMZ and having the deposit number DSM 18541 and variant or mutant strains derived there from. Said variants and mutants retain at least said ability to produce succinic acid (SA) from glycerol, sucrose, maltose, D-glucose, D-fructose and/or D-xylose. In particular, they may also have a 16S rDNA of SEQ ID NO:1 or a sequence which shows a sequence homology of at least 96, 97, 98, 99 or 99.9% and/or a 23S rDNA of SEQ ID NO:2 or a sequence which shows a sequence homology of at least 95, 96, 97, 98, 99 or 99.9%. Variants or mutants of said DD1 strain may have a 23S rDNA different from that of SEQ ID NO:2, while maintaining at least one of the sequence differences as discussed above which distinguishes the 23S rDNA sequence from that of the MBEL 55E strain. As for example, the 132 bp insert is missing in such variants or mutants as well, optionally combined with one or more of the other specific sequence differences depicted in the alignment of Annex 1.

According to another embodiment the bacterial strain of the invention is converting at least one carbon source selected from sucrose, maltose, D-fructose, D-glucose, D-xylose, L-arabinose, D-galactose, D-mannose, and/or glycerol to succinic acid with a yield coefficient YP/S of at least 0.5 g/g up to about 1.28 g/g; as for example a yield coefficient YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g, of at least 1.1 g/g, of at least 1.15 g/g, of at least 1.20 g/g, of at least 1.22 g/g, or of at least 1.24 g/g According to still another embodiment the bacterial strain of the invention is converting at least 28 g/L of glycerol to at least 28.1 g/L succinic acid, with a yield coefficient YP/S of at least 1.0 g/g, or of >1.0 g/g, or of >1.05 g/g, or of >1.1 g/g, or of >1.15 g/g, or of >1.20 g/g, or of >1.22 g/g, or of >1.24 g/g, up to about 1.28 g/g. For example, 28 g/L of glycerol may be converted to up to about 40 or up to about 35 g/L succinic acid.

According to still another embodiment the bacterial strain of the invention is converting at least one carbon source selected from sucrose, maltose, D-fructose, D-glucose, D-xylose, L-arabinose, D-galactose, D-mannose, and/or glycerol to succinic acid with a specific productivity yield of at least 0.6 g gDCW$^{-1}$ succinic acid, or of at least of at least 0.65, of at least 0.7 g gDCW$^{-1}$ h$^{-1}$, of at least 0.75 g gDCW$^{-1}$ h$^{-1}$, or of at least 0.77 g gDCW$^{-1}$ h$^{-1}$ succinic acid.

According to still another embodiment the bacterial strain of the invention is converting at least one carbon source selected from sucrose, maltose, D-fructose, D-glucose, D-xylose, L-arabinose, D-galactose, D-mannose, and/or glycerol to succinic acid with a space time yield for succinic acid of at least 2.2 g/(L h) or of at least 2.5, at least 2.75, at least 3, at least 3.25, at least 3.5 or at least 3.7 g/(L*h) succinic acid.

According to still another embodiment the bacterial strain of the invention is converting at least 28 g/L of at least one carbon source selected from sucrose, maltose, D-fructose, D-glucose, D-xylose, L-arabinose, D-galactose, D-mannose, and/or glycerol to succinic acid with a space-time-yield for succinic acid of at least 2.2 g/(L h), or of at least 2.5, at least 2.75, at least 3, at least 3.25, at least 3.5 or at least 3.7 g/(L*h).

According to another embodiment the bacterial strain of the invention is converting at least one carbon source selected from sucrose, maltose, D-fructose, D-glucose, D-xylose, L-arabinose, D-galactose, D-mannose, and/or glycerol to succinic acid with a specific productivity yield of at least 0.6 g gDCW$^{-1}$ h$^{-1}$ or of at least of at least 0.65 or of at least 0.7 g gDCW$^{-1}$ h$^{-1}$ succinic acid, or of at least 0.77 g gDCW$^{-1}$ h$^{-1}$ succinic acid, and a space-time-yield for succinic acid of at least 2.2 g/(L h), or of at least 2.5, at least 2.75, at least 3, at least 3.25, at least 3.5 or at least 3.7 g/(L*h).

In another embodiment of the claimed bacterial strains as defined above the carbon source is glycerol or a mixture of glycerol and at least one further carbon source selected from sucrose, maltose, D-fructose, D-galactose, D-mannose, D-glucose, D-xylose, and L-arabinose.

The different yield parameters as described herein ("Yield" or YP/S; "Specific Productivity Yield"; or Space-Time-Yield (STY)) are well known in the art and are determined as described for example by Song and Lee, 2006.

"Yield" and "YP/S" (each expressed in mass of product produced/mass of material consumed) are herein used as synonyms.

The specific productivity yield describes the amount of a product, like succinic acid that is produced per h and L fermentation broth per g of dry biomass. The amount of dry cell weight stated as DCW describes the quantity of biologically active microorganism in a biochemical reaction. The value is given as g product per g DCW per h (i.e. g gDCW$^{-1}$ h$^{-1}$).

A further embodiment of the invention relates to a process for the fermentative production of an organic acid or a salt or derivative thereof, which process comprises the steps of:

a) incubating a bacterial strain as defined in one of the preceding claims in a medium containing an assimilable carbon source and cultivating said strain at a temperature in the range of about 10 to 60 or 20 to 50 or 30 to 45° C. at a pH of 5.0 to 9.0 or 5.5 to 8.0 or 6.0 to 7.0 in the presence of carbon dioxide; and b) obtaining said organic acid or salt or derivative thereof from the medium.

Said process may be performed discontinuously or continuously and the course of the acid production may be monitored by conventional means, as for example HPLC or GC analysis.

Preferably, by said process succinic acid (SA) is produced, preferably under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm.

Aerobic conditions may be established by means of conventional techniques, as for example by introducing air or oxygen at a flow rate of, for example, 0.1 to 1 or 0.2 to 0.5 vvm.

If appropriate a slight over pressure of 0.1 to 1.5 bar may be applied.

In said process said assimilable carbon source is preferably selected from glycerol, D-glucose, D-xylose, L-arabinose, D-galactose, D-mannose and mixtures thereof or compositions containing at least one of said compounds, or is selected from decomposition products of starch, cellulose, hemicellulose and/or lignocellulose.

The initial concentration of the assimilable carbon source is preferably adjusted to a value in a range of 5 to 100 g/l and may be maintained in said range during cultivation.

The pH of the reaction medium may be controlled by addition of suitable bases as for example, $NH_4OH$, $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, CaO, $CH_6N_2O_2$, $C_2H_7N$, or other bases and mixtures thereof. The physical condition of the base can either be an aqueous solution, aqueous suspension, gaseous or solid.

Particularly preferred conditions for producing SA are:
Carbon source: Glucose, xylose or maltose and/or glycerol (including crude glycerol)
Temperature: 30 to 45° C.
pH: 6.0 to 7.0, controlled by a base as described above, preferably by a $HCO_3^-$ source such as $Na_2CO_3$, $NaHCO_3$, $Mg(HCO_3)_2$, $Ca(HCO_3)_2$ or, $Mg(OH)_2$, $MgCO_3$, $Ca(OH)_2$, $CaCO_3$.
supplied gas: $CO_2$ In another embodiment the present invention provides a process for the fermentative production of succinic acid or a salt or derivative thereof, which process comprises the steps of:
a) incubating a bacterial strain in a medium containing at least one assimilatable carbon source and cultivating said strain under conditions favoring the formation of the desired organic acid;
b) obtaining said organic acid or salt or derivative thereof from the medium;

and which process is additionally characterized by conversion of at least 28 g/L of glycerol to at least 28.1 g/L succinic acid, with a yield coefficient YP/S of at least 1.0 g/g, or of >1.0 g/g, or of >1.05 g/g, or of >1.1 g/g, or of >1.15 g/g, or of >1.20 g/g, or of >1.22 g/g, or of >1.24 g/g; up to about 1.28 g/g; as for example a yield coefficient YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g, of at least 1.1 g/g, of at least 1.15 g/g, of at least 1.20 g/g, of at least 1.22 g/g, or of at least 1.24 g/g. For example, 28 g/L of glycerol may be converted to up to about 40 or up to about 35 g/L succinic acid.

In another embodiment the present invention provides a process for the fermentative production of succinic acid or a salt or derivative thereof, which process comprises the steps of:
a) incubating a bacterial strain in a medium containing at least one assimilatable carbon source and cultivating said strain under conditions favoring the formation of the desired organic acid;
b) obtaining said organic acid or salt or derivative thereof from the medium;

and which process is additionally characterized by
conversion of a carbon source selected from sucrose, maltose, D-fructose, D-glucose, D-xylose, L-arabinose, D-galactose, D-mannose, and/or glycerol to succinic acid with a specific productivity yield of at least 0.6 g gDCW$^{-1}$ h$^{-1}$ succinic acid or of at least of at least 0.65 or of at least 0.7 g gDCW$^{-1}$ h$^{-1}$ succinic acid, or of at least 0.75 g gDCW$^{-1}$ h$^{-1}$ succinic acid, or of at least 0.77 g gDCW$^{-1}$ h$^{-1}$ succinic acid.

In another embodiment the present invention provides a process for the fermentative production of succinic acid or a salt or derivative thereof, which process comprises the steps of:
a) incubating a bacterial strain in a medium containing at least one assimilatable carbon source and cultivating said strain under conditions favoring the formation of the desired organic acid;
b) obtaining said organic acid or salt or derivative thereof from the medium;

and which process is additionally characterized by conversion of a carbon source selected from sucrose, maltose, D-fructose, D-glucose, D-xylose, L-arabinose, D-galactose, D-mannose, and/or glycerol to succinic acid with a space time yield for succinic acid of at least 2.2 g/(L h), or of at least 2.5, at least 2.75, at least 3, at least 3.25, at least 3.5 or at least 3.7 g/(L*h) succinic acid.

In another embodiment the present invention provides a process for the fermentative production of succinic acid or a salt or derivative thereof, which process comprises the steps of:
a) incubating a bacterial strain in a medium containing at least one assimilatable carbon source and cultivating said strain under conditions favoring the formation of the desired organic acid;
b) obtaining said organic acid or salt or derivative thereof from the medium;

and which process is additionally characterized by conversion of at least 28 g/L of a carbon source selected from sucrose, maltose, D-fructose, D-glucose, D-xylose, L-arabinose, D-galactose, D-mannose, and/or glycerol to succinic acid with a space-time-yield for succinic acid of at least 2.2 g/(L h), or of at least 2.5, at least 2.75, at least 3, at least 3.25, at least 3.5 or at least 3.7 g/(L*h).

In another embodiment the present invention provides a process for the fermentative production of succinic acid or a salt or derivative thereof, which process comprises the steps of:
a) incubating a bacterial strain in a medium containing at least one assimilatable carbon source and cultivating said strain under conditions favoring the formation of the desired organic acid;
b) obtaining said organic acid or salt or derivative thereof from the medium;

and which process is additionally characterized by conversion of a carbon source selected from sucrose, maltose, D-fructose, D-glucose, D-xylose, L-arabinose, D-galactose, D-mannose, and/or glycerol to succinic acid with a specific productivity yield of at least 0.6 g gDCW$^{-1}$ h$^{-1}$ succinic acid or of at least of at least 0.65 or of at least 0.7 g gDCW$^{-1}$ h$^{-1}$ succinic acid, or of at least 0.75 g gDCW$^{-1}$ h$^{-1}$ succinic acid, or of at least 0.77 g gDCW$^{-1}$ h$^{-1}$ succinic acid and a space-time-yield for succinic acid of at least of at least 2.2 g/(L h), or of at least 2.5, at least 2.75, at least 3, at least 3.25, at least 3.5 or at least 3.7 g/(L*h).

In another embodiment of the above identified processes of producing succinic acid the carbon source is glycerol or a mixture of glycerol and at least one further carbon source selected from sucrose, maltose, D-fructose, D-galactose, D-mannose, D-glucose, D-xylose, and L-arabinose.

Further preferred conditions will be derivable from the attached examples and figures.

Succinic acid and/or succinic acid salts produced may be isolated in conventional manner by methods known in the art, as for example cristallization, filtration, electrodialysis, chromatography. For example, they may be isolated by precipitating as a calcium succinate product in the fermentor during the fermentation by using calcium hydroxide, -oxide, -carbonate or hydrogencarbonate for neutralization and filtration of the precipitate.

The desired succinic acid product is recovered from the precipitated calcium or succinate by acidification of the succinate with sulfuric acid followed by filtration to remove the calcium sulfate (gypsum) or which precipitates. The resulting solution may be further purified by means of ion exchange chromatography in order to remove undesired residual ions.

Another embodiment of the invention relates to a process for the production of succinic acid and/or succinic acid salts, in particular ammonium salts, which method comprises the fermentative production of succinic acid as defined above and controlling the pH with a suitable base, in particular inorganic base, like ammonia, or an aqueous solution thereof.

Another embodiment of the invention relates to a process for the production of tetrahydrofuran (THF) and/or 1,4-butanediol (BDO) and/or gamma-butyrolactone (GBL) which comprises
a) the fermentative production of succinic acid and/or succinic acid salts, e.g. ammonium salts as defined above, and
b1) either the direct catalytic hydrogenation of the obtained free acid to THF and/or BDO and/or GBL or
b2) the chemical esterification of obtained free succinic acid and/or succinic acid ammonium salts to its corresponding di-loweralkyl ester and subsequent catalytic hydrogenation of said ester to THF and/or BDO and/or GBL.

Lower alkyl preferably represent a straight chain or branched $C_1$-$C_6$-, preferably $C_1$-$C_4$-alkyl residue, in particular methyl, ethyl, n-propyl, isopropyl, n-butyl, sec-butyl, isobutyl, tert-butyl, as well as n-pentyl and n-nexyl and branched analogues thereof.

Another embodiment of the invention relates to a process for the production of pyrrolidones which comprises
a) the fermentative production of succinic acid ammonium salts as defined above, and
b) the chemical conversion of succinic acid ammonium salts to pyrrolidones in a manner known per se, for example as described in WO-A-2006/066839 (which document is herewith incorporated by reference).

In a preferred embodiment, said glycerol, which is used as assimilable carbon source, is crude glycerol.

More Details on Direct Hydrogenation of SA:

Suitable experimental conditions for performing direct catalytic hydrogenation are well known, and for example, described in U.S. Pat. No. 4,550,185, incorporated herewith by reference.

The SA is hydrogenated in a manner known per se using processes, apparatus and assistants, such as solvents, familiar to the person skilled in the art. In particular, a continuous or batch wise liquid phase hydrogenation is carried out in the presence of a heterogeneous catalyst suitable for the acid hydrogenation. The optimal process parameters can be established by the person skilled in the art without unacceptable effort. For example, the reaction temperature is in the range from about 100 to about 300° C., preferably in the range from about 130 to 285° C., and the pressure is from about 20 to 350 bar, for example from 100 to 250 bar. Catalysts usable for the hydrogenation reaction are known to the person skilled in the art. For example, various palladium/rhenium/carbon catalysts may be used. Solvents usable for the hydrogenation reaction are known to the person skilled in the art. For example, an aqueous solvent medium may be used.

More Details on Esterification of SA Followed by Hydrogenation:

Suitable experimental conditions for performing the chemical esterification, followed by direct catalytic hydrogenation are well known, and for example, described in European Patent application 06007118.0 incorporated herewith by reference.

a) Esterification Process:

The esterification process which may comprise a reactive distillation can be performed using an apparatus known per se in various designs.

For example an esterification plant which is operated in continuous mode can be used which comprises a rectification column with an appropriate number of theoretical stages achieved by installation of trays or packings. The aqueous charge comprising the ammonium salt of SA is fed into the top of the column from a reservoir vessel as soon as a steady-state temperature profile has formed in the column as a result of feeding-in alkanol that is evaporated in the evaporator loop adherent to the sump of the column. The reaction forms a countercurrent flow of descending, ammonium salt-containing liquid and condensate, and ascending, alkanol-containing vapor phase. To catalyze the esterification reaction, a homogeneous catalyst may be added to the ammonium salt initial charge. Alternatively, heterogeneous catalysts may be provided in the column internals. The carboxylic ester formed is liquid under the process conditions and passes via the lower end of the column into the sump of the distillation column and is continuously withdrawn from the sump. Gaseous components, for example azeotropic mixtures comprising alkanol-water and/or ammonia, are removed from the reaction column and hence from the reaction equilibrium at the top of the column.

Further modifications of the above-described specific embodiments can be implemented by the person skilled in the art without unacceptable effort.

Suitable process parameter ranges for the esterification process according to the invention can be determined easily by the person skilled in the art depending on the configuration of the apparatus used, for example type of column internals used, type and amount of the reactants, type and amount of the catalyst used if appropriate. For instance, without being restrictive thereto, individual parameters may be set within the following parameter ranges:

Column temperature: 0-300° C., in particular 40-250° C., or 70-200° C.

Pressure: from 0.1 to 6 bar, in particular standard pressure

Residence time: a few seconds (for example from 1 to 60) up to days (for example from 1 to 5), in particular from a few minutes (for example from 1 to 60) to a few hours (for example from 1 to 15), more preferably from a few minutes (for example from 5 to 20) to 2 h.

b) Hydrogenation Process

The SA esters prepared in accordance with the invention are hydrogenated in a manner known per se using processes, apparatus and assistants, such as catalysts, familiar to the person skilled in the art.

In particular, a continuous or batchwise gas phase hydrogenation is carried out in the presence of a heterogeneous catalyst suitable for the ester hydrogenation. The optimal process parameters can be established by the person skilled in the art for the particular ester without unacceptable effort. For example, the reaction temperature is in the range from about 100 to about 300° C., preferably in the range from about 200 to 280° C., and the pressure is from about 5 to 100 bar, for example from 10 to 50 bar. The molar ratio of reactant to hydrogen is set within the range from about 1:100 to about 1:2000, for example from 1:800 to 1:1500.

Catalysts usable for the inventive hydrogenation reaction are known to the person skilled in the art. For example, various copper catalysts may be used: The prior art describes, for example, the use of reduced copper chromite catalysts which are obtainable under the name 85/1 from Davy Process Technology Ltd., England. However, catalysts particularly suitable in accordance with the invention are supported copper oxide catalysts, the copper oxide being applied to alumina or silica support materials. The examples of the hydrogenation of succinic esters to BOO (1,4-Butanediol)/GBL (gamma-butyrlactone)/THF with copper catalysts are also described in the following thesis: Schlander, January, February 2000, University of Karlsruhe, "Gasphasenhydrierung von Maleinsäuredimethylester zu 1,4-Butandiol, gamma-Butyrolacton and Tetrahydrofuran an Kupfer-Katalysatoren".

More Details on Fermentation Steps:

A fermentation as used according to the present invention can be performed in stirred fermenters, bubble columns and loop reactors. A comprehensive overview of the possible method types including stirrer types and geometric designs can be found in "Chmiel: Bioprozesstechnik: Einführung in die Bioverfahrenstechnik, Band 1". In the process, typical variants available are the following variants known to those skilled in the art or explained, for example, in "Chmiel, Hammes and Bailey: Biochemical Engineering", such as batch, fed batch, repeated fed batch or else continuous fermentation with and without recycling of the biomass. Depending on the production strain, sparging with air, oxygen, carbon dioxide, hydrogen, nitrogen or appropriate gas mixtures can/must be effected in order to achieve good yields.

Before the chemical conversion in the fermentation broth in the process according to the invention, the fermentation broth can be pretreated; for example, the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value. In one embodiment, the fermentation broth can be sterilized or pasteurized.

In a further embodiment, the fermentation broth is concentrated. Depending on the requirement, this concentration can be done batchwise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

In apparatus terms, stirred tanks, falling-film evaporators, thin-film evaporators, forced-flash circulation evaporators and other evaporator types can be utilized in natural or forced circulation mode.

Consequently, the term "fermentation broth" is understood to mean an aqueous solution which is based on a fermentative process and has not been worked up or has been worked up, for example, as described herein.

The present invention will be described in greater detail by means of the following examples. The following examples are for illustrative purposes and are not intendet to limit the scope of the invention.

Example 1

Isolation of DD1

For the isolation a four-step approach was used, comprising the steps of sampling, enrichment cultivation, isolation of pure cultures and test of pure cultures for succinic acid (SA) production.

1. Experimental Approach 1.1. Sampling

Samples were taken from bovine rumen, digested sludge from a municipal sewage plant and pomace, the residue from wine making. These habitats are characterized by relatively high concentrations of organic substances and a $CO_2$-rich atmosphere without oxygen. More detailed information on the samples, their origin and handling is given below.

a) Rumen content was taken from a canulated Holstein cow at the Institut für Tierernährung, University of Hohenheim. In situ-pH and -temperature were 6.7 and 37° C., respectively. The material was filtered through sterile filter cloth, gassed with $CO_2$ and immediately cooled on ice for the transport and processed on the same day.

b) Digested sludge was taken from the digestion tower of the municipal sewage plant in Mannheim-Sandhofen. In situ-pH and -temperature were 7.1 and 36.3° C., respectively. The samples were cooled on ice and processed on the same day. The main components of the gas phase in the sludge are methane and carbon dioxide.

c) Pomace samples were collected in November 2005 from a field in the south west of Germany. Pomace from red grapes (Spätburgunder) was taken from the middle of a big stash. This zone should be anaerobic. Pomace from white grapes (Müller-Thurgau) was taken from a storage container in which the alcoholic fermentation was already in progress.

1.2. Enrichment Cultivation

Enrichment cultivations were performed on different media containing D-glucose, D-xylose and L-arabinose as sole carbon source. The media composition is described below:

TABLE 1

Medium composition for enrichment cultivations.

| Compound | Concentration [g/L] |
| --- | --- |
| C-source[a] | 15 |
| Bacto yeast extrakt (Becton Dickinson) | 5 |
| Bacto peptone (Becton Dickinson) | 5 |
| $(NH_4)_2SO_4$ | 1 |
| $CaCl_2*2H_2O$ | 0.2 |
| $MgCl_2*6H_2O$ | 0.2 |
| NaCl | 1 |
| $K_2HPO_4$ | 3 |
| L-Cystein (reducing agent) | 0.24 |
| $MgCO_3$[b] | 15 |
| Lasalocid[c] | 16 mg/L |
| Monensin[c] | 10 mg/L |
| Amphotericin B[d] | 2.5 mg/L |
| Rumen liquor (optional)[e] | 5 |
| Extract from digested sludge (optional)[f] | 10 |
| Extract from pomace (optional)[f] | 10 |
| Bacto-Agar (for solid media only) | 12 |

[a]D-glucose, D-xylose or L-arabinose
[b]$MgCO_3$ (Riedel-de Haen, product number: 13117 by Sigma-Aldrich Laborchemikalien GmbH, Seelze, Germany).
[c]Stock solution in ethanol.
[d]Stock solution in dimethyl sulfoxide
[e]Rumen liquid was centrifuged. The supernatant was sterile filtered, the sterile filtrate was added to the enrichment trials with rumen content as inoculum.
[f]10 g digested sludge or pomace were mixed with 25 mL distilled water and stirred intensively for 15 min. Rough particles were separated using a filter fleece. The suspensions were sterile filtered, the sterile filtrates were added to the respective enrichment trials.

$MgCO_3$ and water (0.75 g and 40 mL) were autoclaced in 100 mL-serum bottles (121° C., 20 min). Yeast extract, peptone, C-source, $NH_4SO_4$ and $K_2HPO_4$ were all separately autoclaved. For Ca-, Mg- and Na-chlorides one stock solution was prepared which was autoclaved. To ensure that no oxygen was present the following standard procedures were used:

Cultivation media were gassed with sterile and oxygen-free $CO_2$ after autoclaving.

An anaerobic box (Meintrup DWS Laborgeräte GmbH, Länden-Holte, Germany) was used for experiments which had to be performed under anaerobic conditions.

The incubation of the agar plates occurred in anaerobic jars. To ensure anaerobic conditions Anaerocult®A (Merck) was used.

Rumen samples and digested sludge were used undiluted as inoculum. 50 g of solid pomace were diluted in 100 mL 0.9% NaCl solution, filtered to remove rough particles and then used as inoculum.

100 mL serum bottles (Zscheile & Klinger, Hamburg, Germany) were filled with 50 mL medium and 2 mL of the respective inoculum, closed with butyl rubber stoppers (Ochs GmbH, Bovenden/Lenglern, Germany) and gassed with $CO_2$. An overpressure of about 0.8 bar was adjusted. The bottles were incubated in a shaking incubator (160 rpm, shaking diameter: 2.5 cm) at 37° C.

Consumption of glucose, xylose and arabinose and formation of succinic acid and by-products were quantified via HPLC analyses of the undiluted cell free supernatants of the cultivation broth using RI-detection. Broth samples were taken with a sterile syringe through the butyl rubber plug, cell separation was performed by filtration (0.22 μm). A 300×7.8 mm I. D. Column Aminex HPX-87H (Biorad) and 5 mm $H_2SO4$ were used as stationary and mobile phase, respectively. The column temperature was 30° C., the flow rate was 0.5 mL min$^{-1}$.

1.3. Isolation of Pure Cultures

Isolation of pure cultures from the enrichment cultivations was achieved by repeated streaking on agar plates.

1.4. Test of Pure Cultures for Succinic Acid Production

The pure cultures were tested in liquid culture for SA production. Sugar consumption and SA and side product formation were quantified by HPLC. Cultivation and HPLC conditions were the same as those described in the above section 'Enrichment cultivation'.

2. Results

2.1. Recommended Enrichment Conditions

The following table summarizes those experimental conditions, which are recommendable for the enrichment of succinic acid (SA) producers.

TABLE 2

Recommended experimental conditions for the production of SA-producers.

|  | Rumen content | Digested sludge | Pomace |
|---|---|---|---|
| C-source | L-arabinose | L-arabinose[a] | D-glucose, L-arabinose |
| Buffer | $MgCO_3$ | $MgCO_3$ | $MgCO_3$ |
| Antibiotics | lasalocid, monensin | lasalocid, monensin | amphotericin B |
| Incubation time | <16 h | <24 h | <50 h |

[a] glucose and xylose were not tested in trials with digested sludge.

For enrichment of SA producers from rumen content the best C-source is arabinose (3/3 enrichment cultures showing SA production, 0/3 with glucose, 2/3 with xylose). The results are summarized in the following table. Addition of the ionophoric antibiotics lasalocid and monensin to the enrichment medium resulted in substantially higher SA production (1.9-5.4 vs. 0.9-1.2 g/L in 17 h) and lower production of lactic and propionic acid. These results therefore confirm that SA producing microorganisms can indeed be favored by adding these compounds to the enrichment medium (Lee et al., 2002a). $MgCO_3$-buffered enrichment cultures showed higher SA production than trials with TRIS (1.9-5.4 vs. 1.2-1.4 g/L in 17 h). Presumably this is caused by i) the higher buffer capacity of $MgCO_3$, ii) its lower osmotic stress due to lower solubility and iii) by liberation of $CO_2$ from the carbonate-ion, which is necessary for the SA biosynthesis.

TABLE 3

Results of enrichment cultivations for SA producers from rumen content.

| exp no | inc time [h] | C-source | Buffer | anti-obiotics | red. Agent | C-source [g/L] | succinic [g/L] | lactic [g/L] | formic [g/L] | acetic [g/L] | propionic [g/L] | ethanol [g/L] |
|---|---|---|---|---|---|---|---|---|---|---|---|---|
| 1 | 24 | glucose | $MgCO_3$ | — | — | 0.0 | 0.0 | 3.7 | 0.6 | 2.8 | 0.0 | 0.0 |
| 2 | 24 | glucose | $MgCO_3$ | — | — | 0.0 | 0.0 | 3.6 | 0.4 | 2.7 | 0.0 | 0.0 |
| 3 | 24 | glucose | $MgCO_3$ | — | — | 0.0 | 0.0 | 3.9 | 0.4 | 2.6 | 0.0 | 0.0 |
| 4 | 24 | xylose | $MgCO_3$ | — | — | 0.0 | 2.3 | 3.8 | 0.2 | 5.7 | 0.0 | 0.0 |
| 5 | 24 | xylose | $MgCO_3$ | — | — | 0.0 | 0.0 | 3.4 | 0.0 | 2.7 | 0.5 | 0.0 |
| 6 | 24 | xylose | $MgCO_3$ | — | — | 0.0 | 1.8 | 3.4 | 0.0 | 2.7 | 0.0 | 0.0 |
| 7 | 17 | arabinose | $MgCO_3$ | — | — | 1.4 | 0.9 | 7.6 | 0.0 | 1.3 | 1.0 | 0.0 |
| 8 | 17 | arabinose | $MgCO_3$ | — | — | 1.9 | 0.9 | 7.4 | 0.0 | 1.3 | 1.0 | 0.0 |
| 9 | 17 | arabinose | $MgCO_3$ | — | — | 1.2 | 1.2 | 6.8 | 0.0 | 1.5 | 1.2 | 0.0 |
| 10 | 17 | arabinose | $MgCO_3$ | las + mon | — | 1.5 | 3.3 | 0.4 | 3.8 | 3.7 | 0.0 | 2.8 |
| 11 | 17 | arabinose | $MgCO_3$ | las + mon | — | 0.4 | 1.9 | 1.8 | 3.8 | 3.7 | 0.0 | 3.3 |
| 12 | 17 | arabinose | $MgCO_3$ | las + mon | — | 2.4 | 5.4 | 0.0 | 2.9 | 3.6 | 0.0 | 1.8 |
| 13 | 17 | arabinose | TRIS | las + mon | — | 7.2 | 1.2 | 1.3 | 0.0 | 1.4 | 0.4 | 1.5 |
| 14 | 17 | arabinose | TRIS | las + mon | — | 8.0 | 1.4 | 1.3 | 0.0 | 1.3 | 0.4 | 1.4 |
| 15 | 17 | arabinose | TRIS | las + mon | — | 8.8 | 1.4 | 1.2 | 0.0 | 1.1 | 0.3 | 1.2 |

For enrichment of SA producers from digested sludge the only C-source tested was arabinose.

The results are summarized in the following table. These experiments indicated that short incubation times of 24 h or lower are necessary to prevent substrate depletion and SA consumption, presumably by propionic acid producing bacteria: $succinate^{2-} + H_2O \rightarrow propionate^- + HCO_3^-$ (Janssen, 1991).

TABLE 4

Results of enrichment cultivations for SA producers from digested sludge.

| exp no | inc time [h] | C-source | Buffer | anti-obiotics | red. Agent | C-source [g/L] | succinic [g/L] | lactic [g/L] | formic [g/L] | acetic [g/L] | propionic [g/L] | ethanol [g/L] |
|---|---|---|---|---|---|---|---|---|---|---|---|---|
| 1 | 8 | arabinose | $MgCO_3$ | las + mon | — | 13.3 | 0.2 | 0.1 | 0.2 | 0.2 | 0.0 | 1.1 |
| 2 | 8 | arabinose | $MgCO_3$ | las + mon | — | 13.4 | 0.2 | 0.1 | 0.2 | 0.2 | 0.0 | 1.1 |
| 3 | 8 | arabinose | $MgCO_3$ | las + mon | — | 13.1 | 0.2 | 0.1 | 0.2 | 0.2 | 0.0 | 1.1 |
| 1 | 24 | arabinose | $MgCO_3$ | las + mon | — | 0.0 | 1.6 | 1.2 | 3.5 | 3.9 | 0.4 | 3.5 |
| 2 | 24 | arabinose | $MgCO_3$ | las + mon | — | 0.0 | 1.6 | 1.3 | 3.4 | 4.0 | 0.4 | 3.5 |
| 3 | 24 | arabinose | $MgCO_3$ | las + mon | — | 0.0 | 1.7 | 1.3 | 3.1 | 3.8 | 0.4 | 3.4 |
| 1 | 30 | arabinose | $MgCO_3$ | las + mon | — | 0.0 | 0.0 | 1.3 | 3.4 | 4.0 | 1.4 | 3.1 |

TABLE 4-continued

Results of enrichment cultivations for SA producers from digested sludge.

| exp no | inc time [h] | C-source | Buffer | anti-obiotics | red. Agent | C-source [g/L] | succinic [g/L] | lactic [g/L] | formic [g/L] | acetic [g/L] | propionic [g/L] | ethanol [g/L] |
|---|---|---|---|---|---|---|---|---|---|---|---|---|
| 2 | 30 | arabinose | MgCO$_3$ | las + mon | — | 0.0 | 0.9 | 1.4 | 3.4 | 4.1 | 0.9 | 3.2 |
| 3 | 30 | arabinose | MgCO$_3$ | las + mon | — | 0.0 | 0.0 | 1.4 | 3.0 | 4.0 | 1.4 | 3.1 |

Results obtained in enrichment cultures from pomace are summarized in the following table. Enrichment of SA producers from pomace was only successful if pomace from red grapes (Spätburgunder type) were used. It is absolutely necessary to add amphotericin B to the enrichment medium to suppress ethanol production, presumably caused by wine yeasts. Glucose and arabinose were both suitable C-sources but xylose was not. Incubation times that were necessary to unequivocally detect SA production were substantially higher than with sample material from rumen and digested sludge.

Said table indicates that with each of the three sample materials it is possible to receive enrichment cultures producing SA. Enrichment cultures originating from digested sludge showed higher space time yields than those from rumen and pomace (0.4 vs. 0.2 and 0.1 g/[L h]). However, SA-producing isolates were exclusively obtained from SA-producing enrichment cultures with rumen material as inoculum. Apparently isolation of SA producers from digested sludge and pomace requires more sophisticated strategies.

TABLE 5

Results of enrichment cultivations for SA producers from pomace.

| exp no | grape type[a] | inc time [h] | C-source | Buffer | anti-obiotics | red. Agent | C-source [g/L] | succinic [g/L] | lactic [g/L] | formic [g/L] | acetic [g/L] | ethanol [g/L] |
|---|---|---|---|---|---|---|---|---|---|---|---|---|
| 1 | red | 59 | gluose | MgCO$_3$ | las + mon | L-Cystein | 10.8 | 0.0 | 0.0 | 0.0 | 0.1 | 2.0 |
| 2 | red | 59 | gluose | MgCO$_3$ | las + mon | L-Cystein | 10.8 | 0.0 | 0.0 | 0.0 | 0.1 | 2.0 |
| 3 | red | 59 | xylose | MgCO$_3$ | las + mon | L-Cystein | 0.0 | 0.1 | 0.1 | 0.0 | 0.0 | 1.6 |
| 4 | red | 59 | xylose | MgCO$_3$ | las + mon | L-Cystein | 12.7 | 0.1 | 0.1 | 0.0 | 0.0 | 1.5 |
| 5 | red | 59 | arabinose | MgCO$_3$ | las + mon | L-Cystein | 13.4 | 0.1 | 0.1 | 0.0 | 0.0 | 1.6 |
| 6 | red | 59 | arabinose | MgCO$_3$ | las + mon | L-Cystein | 13.3 | 0.0 | 0.1 | 0.0 | 0.0 | 1.5 |
| 7 | white | 59 | gluose | MgCO$_3$ | las + mon | L-Cystein | 0.0 | 0.0 | 0.0 | 0.0 | 0.6 | 6.2 |
| 8 | white | 59 | gluose | MgCO$_3$ | las + mon | L-Cystein | 0.1 | 0.0 | 0.0 | 0.0 | 0.6 | 5.9 |
| 9 | white | 59 | xylose | MgCO$_3$ | las + mon | L-Cystein | 12.8 | 0.0 | 0.2 | 0.0 | 0.0 | 1.5 |
| 10 | white | 59 | xylose | MgCO$_3$ | las + mon | L-Cystein | 13.0 | 0.0 | 0.2 | 0.0 | 0.0 | 1.6 |
| 11 | white | 59 | arabinose | MgCO$_3$ | las + mon | L-Cystein | 13.3 | 0.0 | 0.2 | 0.0 | 0.1 | 1.7 |
| 12 | white | 59 | arabinose | MgCO$_3$ | las + mon | L-Cystein | 13.4 | 0.0 | 0.2 | 0.0 | 0.1 | 1.8 |
| 13 | red | 50 | gluose | MgCO$_3$ | amph. B | L-Cystein | 4.4 | 0.0 | 1.1 | 1.3 | 2.7 | 1.3 |
| 14 | red | 50 | gluose | MgCO$_3$ | amph. B | L-Cystein | 0.0 | 6.9 | 0.0 | 0.3 | 3.2 | 0.4 |
| 15 | red | 50 | xylose | MgCO$_3$ | amph. B | L-Cystein | 0.9 | 0.0 | 3.7 | 3.7 | 2.5 | 1.9 |
| 16 | red | 50 | xylose | MgCO$_3$ | amph. B | L-Cystein | 5.9 | 0.0 | 1.8 | 1.8 | 2.5 | 1.2 |
| 17 | red | 50 | arabinose | MgCO$_3$ | amph. B | L-Cystein | 13.5 | 0.0 | 0.0 | 0.0 | 1.0 | 0.0 |
| 18 | red | 50 | arabinose | MgCO$_3$ | amph. B | L-Cystein | 6.2 | 4.5 | 0.0 | 0.3 | 2.6 | 0.2 |
| 19 | white | 48 | gluose | MgCO$_3$ | amph. B | L-Cystein | 0.0 | 0.0 | 3.8 | 2.1 | 2.9 | 1.6 |
| 20 | white | 48 | gluose | MgCO$_3$ | amph. B | L-Cystein | 0.0 | 0.0 | 3.7 | 1.7 | 5.5 | 1.8 |
| 21 | white | 48 | xylose | MgCO$_3$ | amph. B | L-Cystein | 7.5 | 0.0 | 1.1 | 2.3 | 2.4 | 1.9 |
| 22 | white | 48 | xylose | MgCO$_3$ | amph. B | L-Cystein | 6.8 | 0.0. | 0.7 | 0.0 | 4.4 | 0.8 |
| 23 | white | 48 | arabinose | MgCO$_3$ | amph. B | L-Cystein | 6.2 | 0.0 | 0.6 | 0.2 | 2.8 | 1.2 |
| 24 | white | 48 | arabinose | MgCO$_3$ | amph. B | L-Cystein | 0.3 | 0.0 | 2.4 | 3.5 | 3.8 | 3.5 |

[a]red = pomace from red grapes (Spätburgunder type) as inoculum; white = pomace from white grapes (Müller-Thurgau) as inoculum.

2.2. Best Results from Enrichment Experiments

The best results obtained in enrichment cultures for SA-producers are listed in the following table 6.

TABLE 6

Best results in enrichment cultivations for SA producers.

| | Sample material | | |
|---|---|---|---|
| | Rumen | Digested sludge | Pomace |
| C-source | L-arabinose | L-arabinose | L-arabinose |
| SA [g/L] | 7.1 | 6.9 | 8.4 |
| STY [g/(L h)][a] | 0.2 | 0.4 | 0.1 |
| Yield [g/g][a] | 0.5 | 0.5 | 0.6 |

[a]Space time yield and yield for succinic acid.

2.3. Succinic Acid Producing Isolates

The best isolates (=pure cultures) showing SA production in pure culture experiments and their characteristics are summarized in the following table. The highest SA concentration (8.8 g/L) and space time yield (0.6 g/[L h]) were achieved with DD1, a rumen isolate.

TABLE 7

Characteristics of the best succinc acid (SA) producing isolates.

| Isolate | DD1 | DD1[a] | DD2 |
|---|---|---|---|
| Origin | rumen | rumen | rumen |
| C-source, enr.[b] | L-arabinose | L-arabinose | L-arabinose |
| C-source, pure[b] | L-arabinose | D-glucose | L-arabinose |
| SA [g/L] | 8.8 | 7.3 | 3.5 |
| STY [g/(L h)][c] | 0.6 | 0.5 | 0.1 |
| Yield [g/g][c] | 0.6 | 0.5 | 0.3 |

TABLE 7-continued

Characteristics of the best succinc acid (SA) producing isolates.

| Isolate | DD1 | DD1[a] | DD2 |
|---|---|---|---|
| by products [g/L] | | | |
| formic acid | 3.3 | 3.7 | — |
| acetic acid | 4.5 | 4.2 | 2.7 |
| lactic acid | — | — | 1.5 |
| ethanol | — | — | 2.7 |

[a]Isolate DD1 was tested twice in pure culture, once with glucose and once with arabinose.
[b]C-source, enr. = C-source during enrichment. C-source, pure = C-source during pure culture experiment.
[c]space time yield and yield for succinic acid.

3. Conclusion

Figure 4:
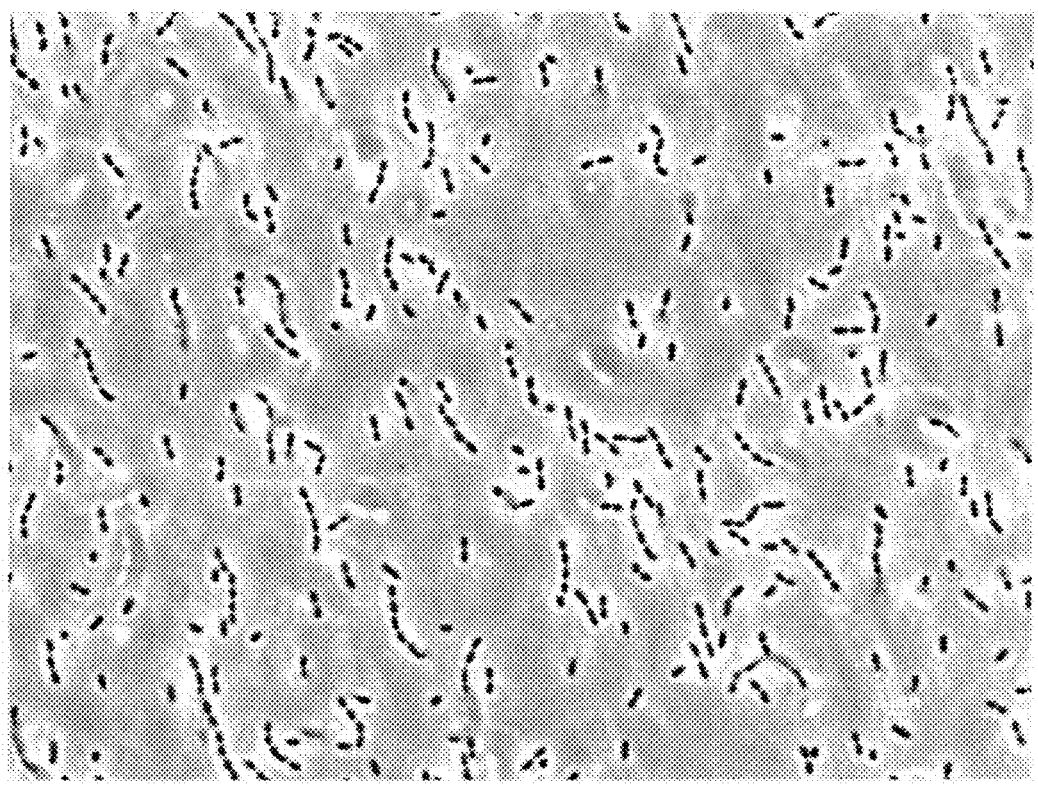
FIG. 4 shows a light microscopic picture of DD1

The established procedure is suitable for enrichment of SA-producers from rumen, digested sludge and pomace. However, SA-producing isolates were exclusively obtained from SA-producing enrichment cultures with rumen material as inoculum. The most promising isolate is the rumen bacterium DD1. It uses glucose and arabinose for SA production. Under not yet optimized conditions almost 9 g/L of SA are produced from 15 g/L of arabinose. FIG. 4 shows a picture of DD1 taken with a light microscope.

Example 2

Cell Bank Preparation of DD1

1. Media Preparation

Composition of the cultivation media is described in table 8.

TABLE 8

Composition of solid and liquid media for the preparation of DD1 cell banks.

| Compound | Concentration [g/L] | Concentration of stock solution [g/L] |
|---|---|---|
| Glucose | varying[a] | 650 |
| Bacto yeast extrakt (Becton Dickinson) | 5 | — |
| Bacto peptone (Becton Dickinson) | 5 | — |
| (NH$_4$)$_2$SO$_4$ | 1 | 500 |
| CaCl$_2$*2H$_2$O | 0.2 | 20 |
| MgCl$_2$*6H$_2$O | 0.2 | 20 |
| NaCl | 1 | 100 |
| K$_2$HPO$_4$ | 3 | 500 |
| MgCO$_3$ | varying[b] | — |
| Bacto-Agar (for solid media only) | 12 | |

[a]Glucose concentrations were 15 g/L (in plates) and 20 or 50 g/L (in liquid media).
[b]MgCO$_3$ Riedel-de Haen, product number: 13117 by Sigma-Aldrich Laborchemikalien GmbH) concentrations were 5 g/L (in plates) and 0 or 30 g/L (in liquid media).

5 g yeast extract, 5 g peptone, MgCO$_3$ and (for solid media) 12 g Bacto-Agar were mixed in 900 mL distilled water and autoclaved (20 min). After cooling down to about 65° C. the missing components were added as sterile stock solutions. Glucose, ammonium sulfate and K$_2$HPO$_4$ were all separately autoclaved. Ca-, Mg- and Na-chlorides were autoclaved together.

2. MCB Preparation

Two agar plates were freshly inoculated with DD1 and incubated at 37° C. in an anaerobic jar (Anaerocult A, Merck) over night. The biomass was taken off the plates and re-suspended in the MgCO$_3$-free liquid medium with 20 g/L glucose to adjust OD$_{600}$≈1.0. Inoculation was performed with 0.5 mL of this cell suspension. Cultivations were performed in 100 mL-serum bottles with gas tight butyl rubber stoppers (Ochs GmbH, Bovenden/Lenglern, Germany) containing 50 mL of the liquid medium with 20 g/L glucose and 30 g/L MgCO$_3$ and a CO$_2$-atmosphere with 0.8 bar overpressure. The serum bottles (in total 10) were incubated at 37° C., a rotary speed of 160 rpm and a shaking diameter of 2.5 cm.

To monitor glucose consumption the cultivation of one bottle was stopped and sampling and HPLC analysis were performed after 0, 3, 4, 5, 7, 8 and 8.5 h. After 8.5 h (the glucose concentration was 3.4 g/L) the cultivation was stopped. Aliquots of 0.5 mL cell suspension and 0.5 mL sterile glycerol were filled in cryovials, mixed and stored for 13 h at −20 and afterwards at −80° C. as MCB. The MCB was tested for purity by streaking a loop of the last cryovial on agar plates for contamination control and checking in liquid culture (media as described table 8) the product spectrum and for contamination (by microscopy). HPLC conditions were the same as those described in example 1.

3. WCB Preparation

One vial of the MCB was used to inoculate a 100 mL-serum bottle with gas tight butyl rubber stopper (see above) containing 50 mL of the liquid medium with 50 g/L glucose. Incubation was performed for 10 h at 37° C. in a shaking incubator (rotary speed: 180 rpm, shaking diameter: 2.5 cm). At the end of the cultivation the glucose concentration was 20 g/L and the pH around 6.5. Aliquots of 0.5 mL cell suspension and 0.5 mL sterile glycerol were filled in cryovials, mixed and stored at −80° C. as WCB. Purity checks were the same as for the MCB. HPLC conditions were the same as those described in example 1.

Example 3

Taxonomic Characterization of DD1

The taxonomic characterization of strain DD1 was performed via 16S- and 23S rDNA analysis which was conducted as described below:

Extraction of genomic DNA, PCR-mediated amplification of the 16S rDNA and purification of PCR products were carried out as described by Rainey et al., 1996. A DNA fragment containing the 23S rDNA was amplified by the same method, using the forward primer 5'-AGTAATAAC-GAACGACACAG-3' (SEQ ID NO: 9) and the reverse primer 5'-AGCCGATTCCCTGACTAC-3' (SEQ ID NO: 10). Purified PCR products were sequenced using the CEQ™DTCS-Quick Start kit (Beckman Coulter) as directed in the manufacturer's protocol. The CEQ™8000 Genetic Analysis System was used for electrophoresis of the sequence reaction products. The ae2 editor (Maidak et al., 1999) was used to align the 16S rDNA sequence of strain DD1 against those of representative members of the γ-subclass of the Proteobacteria available from the EMBL and RDP databases. For the construction of the phylogenetic tree procedures of PHYLIP (Phylogeny Inference Package, version 3.5c., distributed by J. Felsenstein, Department of Genome Sciences, University of Washington, Seattle, USA) were used: Pairwise evolutionary distances were calculated using the method of Jukes and Cantor (1969), the phylogenetic tree was constructed from these distances using the neighbor joining method (Saitou & Nei, 1987).

The 16S rDNA-based phylogenetic tree is depicted in FIG. 1. On the basis of the 16S rDNA analysis the closest relative of strain DD1 is "*Mannheimia succiniciproducens*" MBEL 55E with a similarity of 99.8%. This strain was isolated by scientists of the Korea Advanced Institute of Science and Technology (KAIST) from bovine rumen (Lee et al., 2002a;

Lee et al., 2002b). The amplified 23S rDNA fragment from DD1 was aligned to the 23S rDNA sequences from the "*Mannheimia succiniciproducens*" MBEL 55E (complete genome sequence accession number AE016827) to indicate the difference between the strains.

FIG. 2 shows the 16S rDNA sequence of strain DD1. FIG. 3 shows the 23S rDNA sequence of strain DD1 and an alignment to the 23S rDNA of "*Mannheimia succiniciproducens*" MBEL 55E (complete genome sequence accession number AE016827) is shown in Annex 1.

Example 4

Cell Morphology and Colony Morphology of DD1

One vial of the WCB (example 2) was used to inoculate a 100 mL-serum bottle with gas tight butyl rubber stopper (see above) containing 50 mL of the liquid medium with 50 g/L glucose (composition and preparation as described in example 2). Incubation was performed for 15 h at 37° C. and 170 rpm (shaking diameter: 2.5 cm). At the end of the cultivation the glucose concentration had decreased to about 17 g/L (Measurement via HPLC, conditions as described in example 1). To examine the cell morphology of DD1 single cells were observed using light microscopy. To characterize the colony morphology of DD1 a loop of the cell suspension was streaked on Brain Heart Infusion plates (Bacto Brain Heart Infusion, product number: 237500 solidified with 12 g/L Bacto Agar, product number: 214010; both by Becton, Dickinson and Company) and incubated aerobically and anaerobically (Anaerocult A, Merck) at 37° C.

Cells of DD1 appear as rods that occur singly, in pairs or short chains (see FIG. 4). After 24 h of incubation colonies were circular; white-yellow, translucent and 0.5-1 µm (aerobic growth) and 1-2 µm (anaerobic growth) in diameter.

Example 5

Utilization of Different C-Sources

Utilization of different C-sources by DD1 was tested under the conditions described by Lee et al., 2002a.

1. Medium Preparation

Composition of the cultivation medium is described in table 9.

TABLE 9

Composition of the medium for the tests for utilization of different C-sources.

| Compound | Concentration [g/L] | Concentration of stock solution [g/L] |
|---|---|---|
| C-source | 10 | 250 |
| Bacto yeast extrakt (Becton Dickinson) | 5 | 100 |
| Polypeptone peptone (Becton Dickinson) | 10 | 100 |
| $(NH_4)_2SO_4$ | 2 | 500 |
| $CaCl_2*2H_2O$ | 0.2 | 20 |
| $MgCl_2*6H_2O$ | 0.2 | 20 |
| NaCl | 2 | 100 |
| $K_2HPO_4$ | 3 | 500 |
| $MgCO_3$ (Riedel-de Haen 13117) | 10 | — |

Yeast extract, polypeptone and $MgCO_3$ were autoclaved together. After cooling down the missing components were added as sterile stock solutions. Glucose and the other C-sources, ammonium sulfate and $K_2HPO_4$ were all separately autoclaved. Ca-, Mg- and Na-chlorides were autoclaved together. $Na_2S*9H_2O$ was added to a final concentration of 1 mg/L to ensure anaerobic conditions.

2. Cultivations and Analytics

For growing the seed culture one vial of the WCB was used to inoculate a 100 mL-serum bottle with gas tight butyl rubber stopper (see above) containing 50 mL of the liquid medium described in table 9 but with 20 g/L glucose and a $CO_2$-atmosphere with 0.8 bar overpressure. Incubation was performed for 13 h at 37° C. and 160 rpm (shaking diameter: 2.5 cm). The cell suspension was centrifuged (Biofuge primo R, Heraeus,) with 5000 g for 5 minutes and the cell pellet was washed and then resuspended in 50 mL medium without a carbon source and without $MgCO_3$ to generate a glucose-free inoculum (all steps at room temperature and in the anaerobic chamber).

The main cultures were grown in 100 mL-serum bottles containing in 50 mL liquid medium with 10 g/L of the respective C-source (D-mannitol, D-fructose, D-xylose, sucrose, maltose, lactose, xylitol, inositol, D-sorbitol, glycerol, L-arabinose, D-galactose or D-mannose) and a $CO_2$-atmosphere with 0.8 bar overpressure. For the test for glycerol utilization the quality 'Glycerol 99%, puriss.' (Riedel-de Haen, product numer: 15523-1 L-R by Sigma-Aldrich Laborchemikalien GmbH, Seelze, Germany) was used. Inoculation was performed with 1.5 mL of the glucose-free inoculum. The bottles were incubated at 37° C., and 160 rpm (shaking diameter: 2.5 cm). Utilization of the respective C-source by DD1 was regarded as positive when at least 3 g/L of the C-source were consumed within 24 h. To verify the results obtained in the main culture 1 mL of the respective main culture was used to inoculate 50 mL of fresh cultivation medium with 10 g/L of the respective C-source. The results were therefore confirmed in two subsequent main cultivations. Consumption of the C-sources was quantified via HPLC as described in example 1. When glycerol was measured the column temperature was adjusted to 50° C. to achieve a sufficient separation of SA, lactic acid and glycerol which have similar retention times.

3. Results

The results are summarized in the following table 10.

TABLE 10

Utilization of different C-sources by DD1 and MBEL 55E.

| C-source | DD1[a] | MBEL 55E[b] |
|---|---|---|
| Mannitol | + | + |
| Fructose | + | + |
| Xylose | + | + |
| Sucrose | + | + |
| Maltose | + | + |
| Lactose | + | + |
| Xylitol | − | − |
| Inositol | − | − |
| Sorbitol | − | − |
| Glycerol | + | − |
| Arabinose | + | ND |
| Galactose | + | ND |
| Mannose | + | ND |

[a]Analyses for consumption of each C-source after 24 h. Cultivations were conducted as duplicates.
[b]data from data from Lee et al., 2002a. ND = not determined.

Said table shows that the C-source utilization pattern of the two strains differs with respect to glycerol. DD1 can metabolize glycerol which is not used by MBEL 55E.

In addition to sucrose, D-glucose and D-fructose DD1 utilizes D-xylose, L-arabinose, D-galactose and D-mannose. Hence all types of monosaccharides in lignoellulose (Kamm et al., 2006; Lee, 1997) are utilized by DD1. Utilization of L-arabinose, D-galactose and D-mannose by MBEL55E was not tested by Lee et al., 2002a.

Example 6

SA and by-Product Formation from Glycerol and Different Hexoses and Pentoses DD1's succinic acid (SA) productivity on glycerol, D-xylose, L-arabinose, D-galactose and D-mannose was evaluated in serum bottle trials with 10 g/L of the respective C-source (10 g/L glucose as reference).

1. Medium Preparation

Composition and preparation of the cultivation media were the same as in example 2 (seed culture) and example 5 (main cultures).

2. Cultivations and Analytics

Growth of the seed culture in liquid medium with 50 g/L glucose and 30 g/L $MgCO_3$ was done as described in example 2. Preparation of the glucose-free inoculum was performed as described in example 5.

Growth of the main cultures with 10 g/L glycerol, sucrose, D-xylose, D-Fructose, L-arabinose, D-galactose, D-mannose or D-glucose and 10 g/L $MgCO_3$ was done as described in example 5. Consumption of the respective C-source and production of SA and by-products were quantified by HPLC as described in example 5.

3. Results

In the following table 11 the results are summarized.

TABLE 11

SA and by-product formation from glycerol and different sugars by DD1.

|  | glyc | suc | gluc | fruc | xyl | ara | gal | man |
|---|---|---|---|---|---|---|---|---|
| $t_c$ [h][a] | 9 | 4 | 4 | 4 | 6 | 6 | 6 | 5 |
| $\Delta C_{CS}$ [g/L][b] | −5.3 | −9.8 | −9.3 | −9.4 | −7.6 | −7.8 | −7.1 | −8.1 |
| $\Delta C_{SA}$ [g/L][c] | +6.4 | +5.8 | +5.7 | +4.8 | +4.6 | +4.9 | +4.5 | +4.9 |
| $\Delta C_{LA}$ [g/L][c] | 0 | +0.1 | 0 | +0.4 | 0 | 0 | 0 | 0 |
| $\Delta C_{FA}$ [g/L][c] | +0.4 | +2.0 | +1.8 | +2.3 | +1.9 | +1.6 | +1.2 | +1.8 |
| $\Delta C_{AA}$ [g/L][c] | +0.3 | +2.8 | +2.8 | +2.8 | +2.6 | +2.4 | +2.1 | +2.7 |
| STY [g/(L h)][d] | 0.7 | 1.5 | 1.4 | 1.2 | 0.8 | 0.8 | 0.8 | 1.0 |
| Yield [g/g][d] | 1.2 | 0.6 | 0.6 | 0.5 | 0.6 | 0.6 | 0.6 | 0.6 |

[a]cultivation time.
[b]consumption of carbon source.
[c]formation of succinic, lactic, formic and acetic acid.
[d]space time yield and yield for succinic acid.

Table 11 shows that in all cases substantial SA-amounts are formed. SA production from glycerol (glyc) instead of sucrose (suc), D-glucose (gluc), D-fructose (fruc), D-xylose (xyl), L-arabinose (ara), D-galactose, (gal) or D-mannose (man) by DD1 has two obvious advantages: i) a substantially higher yield, ii) a substantially lower formic and acetic acid formation. On the other hand the SA productivity (space time yield) with glycerol is slightly lower than with the sugars. However, DD1's SA productivity with glycerol is substantially higher than the value obtained with *Anaerobiospirillum succiniciproducens* by Lee et al., 2001 (0.14 g SA/[L h]).

Especially the substantially higher Yield achieved with glycerol is a very interesting result: It can contribute to a clear reduction of production cost for fermentative succinic acid, succinic acid salts and BDO/GBL/THF or pyrrolidones made from it, respectively—in particular if the cheap crude glycerol from biodiesel plants can be applied.

Example 7

SA and by-Product Formation from Different Crude Glycerols

DD1's SA productivity on different crude glycerols (C1 to C3) was evaluated in serum bottle trials with 10 g/L of the respective glycerol (10 g/L pure glycerol [P1] as reference).

1. Medium Preparation

The medium composition is described in the following table 12.

TABLE 12

Medium composition for the test on SA formation from different crude glycerols.

| Compound | Concentration [g/L] | Concentration of stock solution [g/L] |
|---|---|---|
| C-source | varying[a] | varying |
| Bacto yeast extrakt (Becton Dickinson) | 5 | 100 |
| Bacto peptone (Becton Dickinson) | 5 | 100 |
| $(NH_4)_2SO_4$ | 1 | 500 |
| $CaCl_2 * 2H_2O$ | 0.2 | 20 |
| $MgCl_2 * 6H_2O$ | 0.2 | 20 |
| NaCl | 1 | 100 |
| $K_2HPO_4$ | 3 | 500 |
| $MgCO_3$ (Riedel-de Haen 13117) | 30 | — |

[a]Concentrations were 50 g/L of glucose in the seed culture and 10 g/L of the respective glycerol in the main culture.

$MgCO_3$ and water (1.5 g and 40 mL) were sterilized in 100 mL-serum bottles (121° C., 20 min). After cooling down separate sterile solutions of the other compounds were added. Yeast extract, peptone, ammonium sulfate and $K_2HPO_4$ were all separately sterilized by filtration of the respective stock solution. For Ca-, Mg- and Na-chlorides one stock solution was prepared which was sterilized by filtration. Glucose and the different glycerols were all separately sterilized (121° C., 20 min). For the reference trial with pure glycerol (P1) the quality 'Glycerol 99%, puriss.' (Riedel-de Haen, product numer: 15523-1L-R) by Honeywell Specialty Chemicals Seelze GmbH, Seelze, Germany, was used.

2. Cultivations and Analytics

The seed culture was grown in a 100 mL-serum bottle with gas tight butyl rubber stopper (see above) containing 50 mL of the medium described in table 12 with 50 g/L glucose and a $CO_2$-atmosphere with an overpressure of 0.8 bar. Inoculation was conducted with 1 mL of the WCB (example 2). Incubation was performed for 15 h at 37° C. and 170 rpm (shaking diameter: 2.5 cm). At the end of the cultivation the glucose concentration had decreased to about 17 g/L.

The cell suspension was centrifuged (Biofuge primo R, Heraeus) with 5000 g for 5 minutes and the cell pellet was washed and then resuspended in 50 mL of the medium without glucose and without $MgCO_3$ to generate a glucose-free inoculum.

The main cultures were grown in 100 mL-serum bottles containing in 50 mL of the medium with 10 g/L of the respective glycerol and a $CO_2$-atmosphere with 0.8 bar overpressure. Inoculation was performed with 2.0 mL of the glucose-free inoculum. The bottles were incubated for 9 h at 37° C., and 170 rpm (shaking diameter: 2.5 cm).

Consumption of the respective C-source (glucose in seed culture, glycerol in main culture) and production of SA and by-products was measured by HPLC as described in example 5.

3. Results

In the following table 13 the results are summarized.

TABLE 13

SA and by-product formation from different glycerols by DD1.

| | Glycerol type | | | |
|---|---|---|---|---|
| | C1 | C2 | C3 | P1 |
| Producer[a] | ecoMotion | Biopetrol | Glacon Chemie | Sigma-Aldrich |
| Purity [%][b] | 90 | 42 | 76 | 99 |
| $t_c$ [h][c] | 9 | 9 | 9 | 9 |
| $\Delta C_{GI}$ [g/L][d] | −6.3 | −6.9 | −6.5 | −5.4 |
| $\Delta C_{SA}$ [g/L][e] | +7.6 | +8.4 | +7.4 | +6.2 |
| $\Delta C_{LA}$ [g/L][e] | 0 | +0.1 | +0.1 | +0.1 |
| $\Delta C_{FA}$ [g/L][e] | +0.3 | +0.3 | +0.3 | +0.3 |
| $\Delta C_{AA}$ [g/L][e] | +0.3 | +0.5 | +0.3 | +0.3 |
| STY [g/(L h)][f] | 0.8 | 0.9 | 0.8 | 0.7 |
| Yield [g/g][f] | 1.2 | 1.2 | 1.1 | 1.1 |

[a] ecoMotion GmbH, Sternberg, Germany; Biopetrol Schwarzheide GmbH, Schwarzheide, Germany; Glacon Chemie, Merseburg, Germany: Riedel de Haen (product number: 15523-1L-R) by Sigma-Aldrich Laborchemikalien GmbH, Seeize, Germany.
[b] Producer's analysis.
[c] cultivation time.
[d] consumption of glycerol.
[e] formation of succinic, lactic, formic and acetic acid.
[f] space time yield and yield for succinic acid.

Table 13 shows that after 9 h the SA concentration and hence the STY obtained with the crude glycerols C1 to C3 (7.4 to 8.4 g SA/L and 0.8 to 0.9 g SA/[L h]) is in all cases higher than the respective values obtained with the pure glycerol P1 (6.2 g SA/L and 0.7 g SA/[L h]). The crude glycerols have therefore in addition to the lower price the advantage of better productivity. The Yields obtained with the crude glycerols C1 to C3 (1.1 to 1.2 g SA/g glycerol) are similar to the respective value obtained with the pure glycerol P1 (1.1 g SA/g glycerol).

Example 8

Ammonia and Glucose Tolerance of DD1

A common approach for the fermentative production of succinic acid and/or succinic acid ammonium salts from glucose would be a $NH_3$-controlled fed batch cultivation with a certain initial glucose level. This set-up requires both $NH_3$/$NH_4OH$—and glucose tolerance of the strain. To test DD1 for these properties batch cultivations with $NH_4OH$ as pH-control agent and varying glucose levels were performed.

1. Medium Preparation

Composition of the cultivation medium is described in table 14.

TABLE 14

Medium composition for pH-controlled batch cultivations with varying glucose levels.

| Compound | Concentration [g/L] | Concentration of stock solution [g/L] |
|---|---|---|
| Glucose | Varying[a] | 650 |
| Bacto yeast extrakt (Becton Dickinson) | 5 | — |
| Bacto peptone (Becton Dickinson) | 5 | — |
| $(NH_4)_2SO_4$ | 1 | 500 |
| $CaCl_2 \cdot 2H_2O$ | 0.2 | 20 |
| $MgCl_2 \cdot 6H_2O$ | 0.2 | 20 |
| NaCl | 1 | 100 |
| $K_2HPO_4$ | 3 | 500 |
| L-Cystein | 0.24 | 120 |
| $MgCO_3$ (Riedel-de Haen 13117) | 2 | — |

[a] The initial glucose concentration in the preculture was 50 g/L and in the fermentors 25, 50 or 75, respectively.

Yeast extract, peptone and $MgCO_3$ were autoclaved together in the fermentors and serum bottles. Glucose, ammonium sulfate and $K_2HPO_4$ were all separately autoclaved. Ca-, Mg- and Na-chlorides were autoclaved together. After cooling down the fermentors and serum bottles the missing components were added as sterile stock solutions. For the precultures the same medium composition was used but $MgCO_3$ was adjusted to 30 g/L.

2. Cultivations and Analytics

Precultures were grown anaerobically in 100 mL-serum bottles with gas tight butyl rubber stoppers (Ochs GmbH, Bovenden/Lenglern, Germany) containing 50 mL preculture medium at 37° C. in a shaking incubator (rotary speed: 160 rpm, shaking diameter: 2.5 cm). Inoculation of the precultures was performed with 1 mL of a DD1-working cell bank in the anaerobic chamber (MAKS MG 500, meintrup-dws). Immediately after the inoculation the gas atmosphere (80% $N_2$, 15% $CO_2$ and 5% $H_2$) was substituted by pure $CO_2$ with an overpressure of about 0.8 bar. After 16 to 18 h of incubation two bottles were pooled in the anaerobic box and in each case 15 mL were used to inoculate the fermentors (Sixfors, Infors, Switzerland) containing 300 mL cultivation medium which had been gassed over night with $CO_2$ to ensure oxygen-free conditions. Cultivation temperature was 37° C., the pH of 6.5 was maintained with 25% $NH_4OH$. $CO_2$-gas stream and stirrer speed were adjusted to 0.1 L/min and 500 rpm, respectively. Consumption of glucose and production of SA were quantified by HPLC as described in example 1.

3. Results

Figure 5:
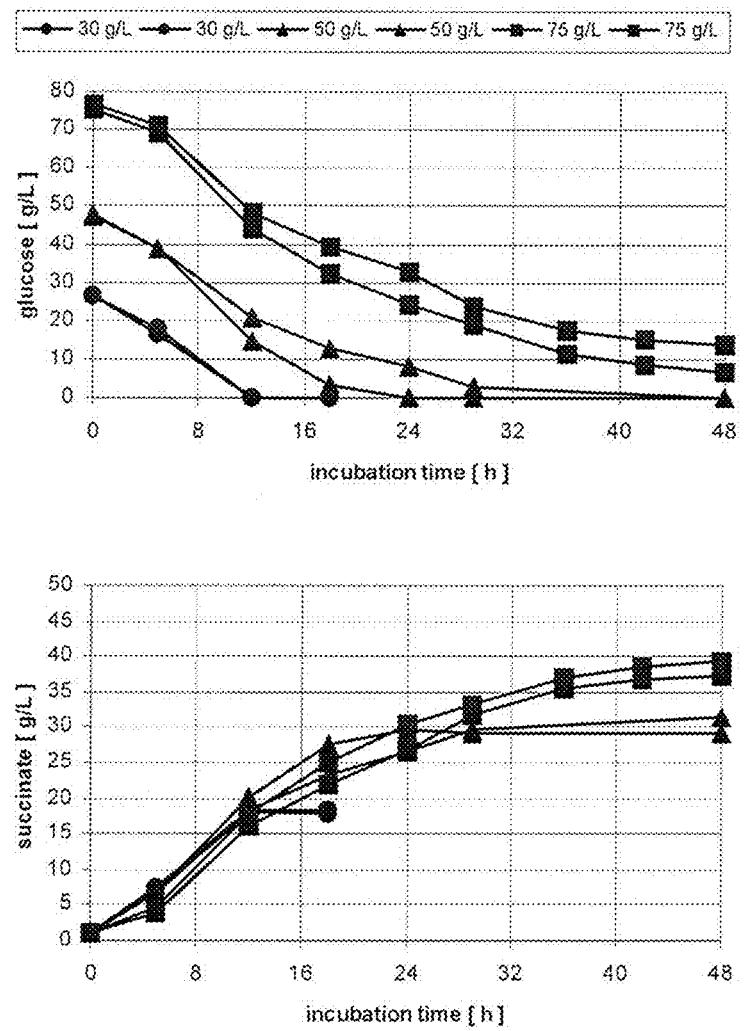
FIG. 5 shows $NH_4OH$-controlled batch cultivations of DD1 at different initial glucose concentrations

The results are shown in FIG. 5.

In $NH_4OH$-controlled batch cultivations with glucose up to 40 g/L SA are formed within 48 h. DD1 has therefore a strong synthesis potential for succinic acid and/or succinic acid ammonium salts which are favourable for the chemical conversion to THF/BDO/GBL and pyrrolidones (WO-A-2006/066839).

The initial SA production rate in the trials with 75 g/L of glucose is slightly lower than in the trials with 50 and 25 g/L. However, between 6 and 12 h there is no such difference anymore indicating that substrate inhibition is not an issue at glucose levels of up to 75 g/L.

Example 9

Effect of Cultivation Temperature and -pH on SA Formation by DD1

In this experiment cultivation temperature and -pH were varied in $NH_4OH$-controlled batch cultivations with 75 g/L glucose.

1. Medium Preparation

Apart from the constant glucose concentration medium composition and preparation were the same as those in example 8 'Ammonia and glucose tolerance of DD1'.

2. Cultivations and Analytics

Apart from the different cultivation temperatures and -pH-values tested the experimental conditions of the cultivations and HPLC analyses were identical to those in example 8 'Ammonia and glucose tolerance of DD1'.

3. Results

Figure 6:
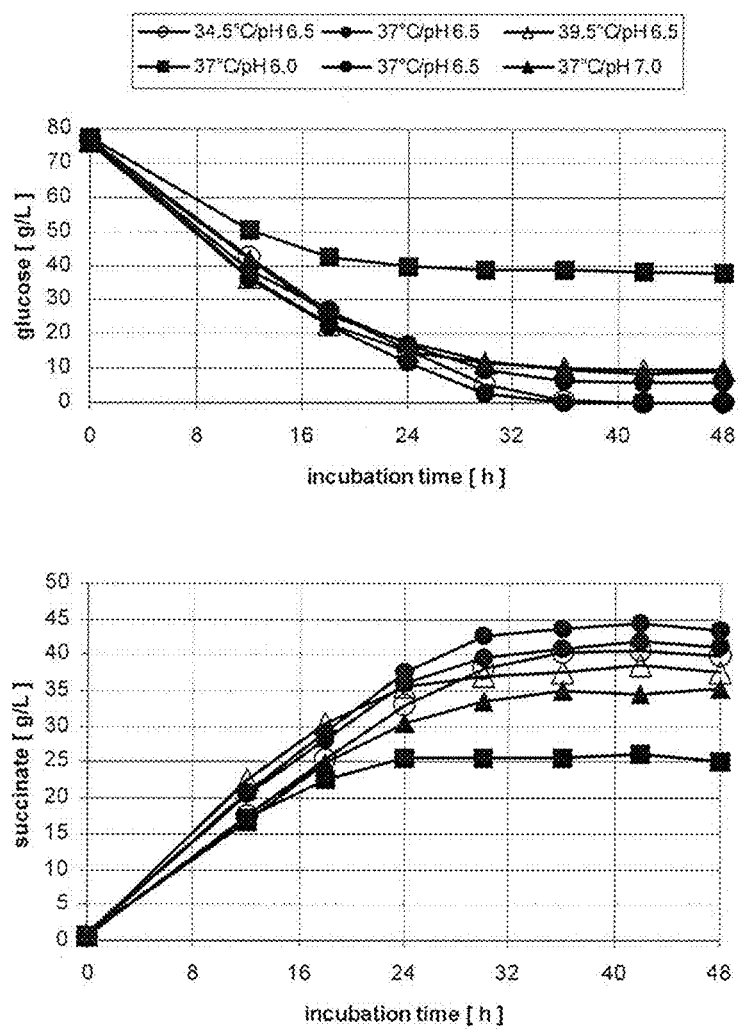
FIG. 6 shows $NH_4OH$-controlled batch cultivations of DD1 at different temperature- and pH-values.

The results are shown in FIG. 6. FIG. 6 shows that the two trials at 37° C. and pH 6.5 are very similar with respect to both, glucose consumption and SA production indicating a low variability. On the basis of this variability the trials, which were performed at pH 6.5 show that between 34.5 and 39.5° C. the cultivation temperature has no impact on the process performance. However, the trials at 37° C. indicate that a pH-reduction by 0.5 units results in a clear and a pH-increase by 0.5 units results in a slight drop of the SA productivity. On the basis of these results further cultivations of DD1 were—if pH-control was possible—performed at pH 6.5.

Example 10

Effect of Complex Media Ingredients on DD1 Cultivation

Enrichment and isolation of DD1 was performed in a cultivation medium containing 5 g/L yeast extract and 5 g/L peptone. Therefore the first experiments with DD1 were conducted in a medium with these compounds. Since they contribute to cost for raw materials and introduce additional impurities, different media compositions were tested in which yeast extract and peptone are reduced and substituted by the cheaper corn steep liquor (Solulys L48L, Roquette), respectively. The initial media composition of the trials is indicated by figures (representing the concentration, i.e. 2, 5, 15 or 25 g/L) and letters (representing the respective complex compound, i.e. yeast extract, peptone or corn steep liquor).

1. Medium preparation

Apart from the respective modification of the yeast extract—and peptone—concentration and the additional corn steap liquor medium composition and—preparation were the same as those in example 8 'Ammonia and glucose tolerance of DD1'. The batch concentration of glucose was 50 g/L in all trials.

2. Cultivations and Analytics

The experimental conditions were identical to those in example 8 'Ammonia and glucose tolerance of DD1'. All cultivations were performed at 37° C., the cultivations in fermentors were maintained at pH 6.5 with 25% $NH_4OH$. HPLC analyses were performed as described in example 8.

3. Results

Figure 7:
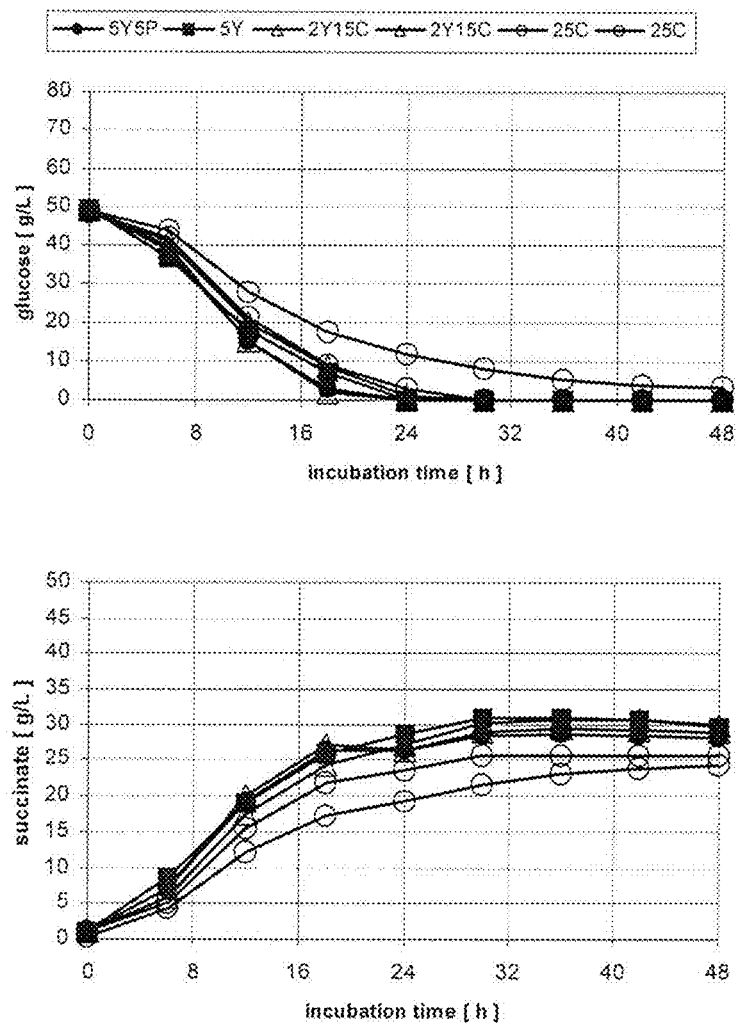
FIG. 7 shows $NH_4OH$-controlled batch cultivations of DD1. Figures represent initial levels [g/L] of yeast extract (Y), peptone (P) and corn steep liquor (C).

The results are shown in FIG. 7. Comparison of the trials '5Y5P' and '5Y' shows that peptone can be omitted without any negative effect on the SA production. The partial substitution of yeast extract by CSL does not result in reduced succinic acid production, either (trial '5Y' vs. trials '2Y15C'). However, the complete substitution of yeast extract by CSL results in moderate productivity losses.

Figure 8:
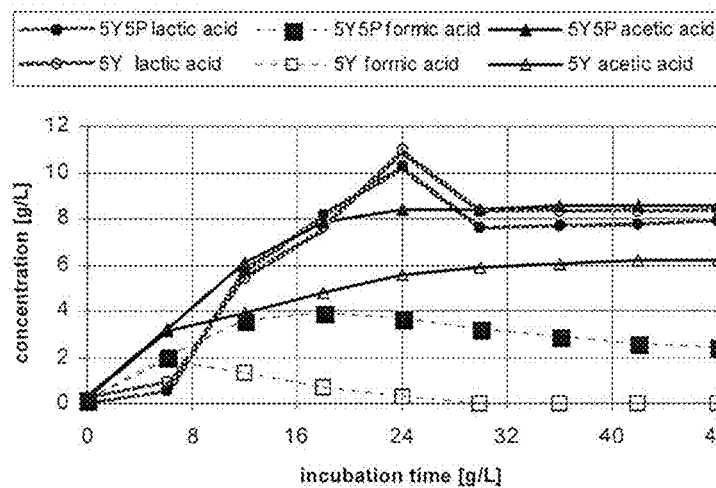
FIG. 8 shows byproducts as obtained in $NH_4OH$-controlled batch cultivations of DD1 with and without peptone.

The by-product spectrum of the trials '5Y5P' and '5Y' is shown in FIG. 8. FIG. 8 shows that omission of peptone in the cultivation medium results in substantially lower concentrations of formic and acetic acid, whereas the concentrations of lactic acid were comparable in both trials. This experiment indicates potential for medium improvement by i) reduction of raw material cost, ii) reduction of impurities introduced by the medium compounds and iii) reduction of side product formation during the cultivation.

Example 11

DD1's Relation to Oxygen

Since the fermentative SA production is a process that depends on anaerobic conditions, the cultivation of DD1 for SA production has to be performed in the absence of oxygen. However, it is very important to know if DD1 tolerates the presence of oxygen, too. If this is the case the strain can be handled under aerobic conditions which makes the lab work a lot easier and faster. Therefore strain DD1 was tested in shake flask experiments with glucose.

1. Medium Preparation

Medium composition and preparation were the same as described in table 8.

2. Cultivations and Analytics

Anaeorbic seed cultures were grown in 100 mL-serum bottles with gas tight butyl rubber stoppers (see above) containing 50 mL medium with 50 g/L of glucose and 30 g/L of $MgCO_3$ and a CO2-atmosphere with an overpressure of 0.8 bar at 37° C. and 160 rpm (shaking diameter: 2.5 cm) for 16 h. Inoculation was performed with 1 mL of the WCB (example 2). 7.5 mL of these precultures were used to inoculate the aerobic main cultures.

Aerobic main cultures (150 mL medium with 60 g/L of glucose and 80 g/L of $MgCO_3$) were grown at 37° C. and 200 rpm (shaking diameter: 2.5 cm) in 500 mL Erlenmeyer flasks with two baffles and cotton plugs. Substrate consumption and product formation were measured by HPLC as described in example 1.

3. Results

Figure 9:
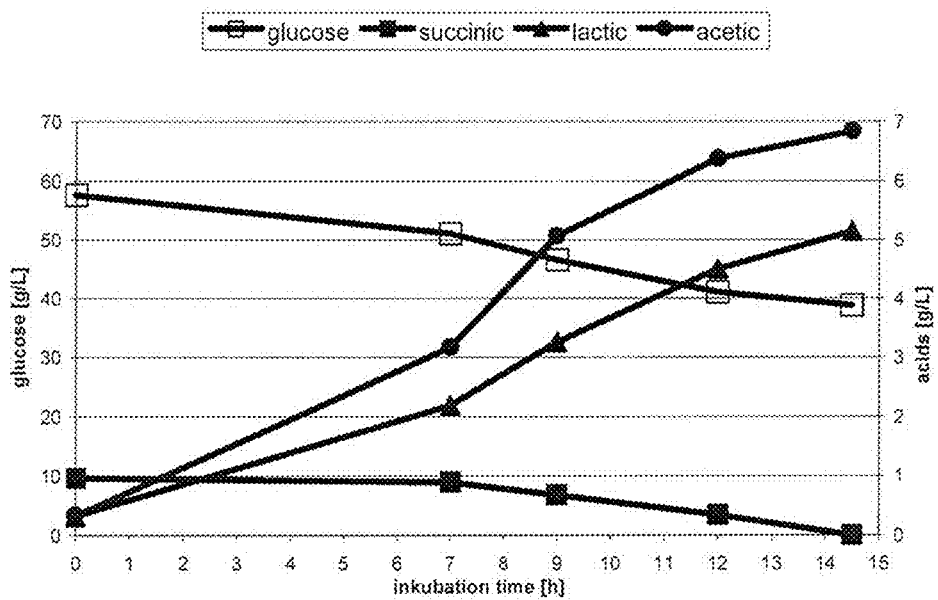
FIG. 9 shows the results of aerobic batch cultivations of DD1 with glucose as C-source.

The results are shown in FIG. 9. The results clearly show aerobic glucose consumption by strain DD1. The main products are acetic and lactic acid which are the dominating products of aerobically grown cells of "*Mannheimia succiniciproducens*" MBEL 55E, too (Lee et al., 2002a). Initial SA levels are introduced by the anaerobic preculture and are widely consumed after 15 h of cultivation. The data clearly show that DD1 is oxygen tolerant.

Example 12

Test of DD1 Under Conditions Described by KAIST

The closest relative of DD1 is "*Mannheimia succiniciproducens*" MBEL 55E, a strain isolated by KAIST (see above). To compare DD1 with said strain the cultivation experiment described by KAIST (FIG. 2*b* in Lee et al., 2002a and FIG. 3 in Lee et al., 2002b) was performed with DD1.

1. Medium Preparation

The composition of the cultivation medium was identical to the respective experiment of Lee et al., 2002b and is described in the following table 15.

TABLE 15

Medium composition for batch cultivations of DD1 under the conditions described by Lee et al., 2002b.

| Compound | Concentration [g/L] | Concentration of stock solution [g/L] |
|---|---|---|
| Glucose | 20 | 650 |
| Bacto yeast extrakt (Becton Dickinson) | 5 | — |
| Polypeptone peptone (Becton Dickinson) | 5 | — |
| $(NH_4)_2SO_4$ | 1 | 500 |

TABLE 15-continued

Medium composition for batch cultivations of DD1 under the conditions described by Lee et al., 2002b.

| Compound | Concentration [g/L] | Concentration of stock solution [g/L] |
|---|---|---|
| $CaCl_2*2H_2O$ | 0.2 | 20 |
| $MgCl_2*6H_2O$ | 0.2 | 20 |
| NaCl | 1 | 100 |
| $K_2HPO_4$ | 3 | 500 |
| $MgCO_3$ (Riedel-de Haen 13117) | 10 | — |

Yeast extract, peptone and $MgCO_3$ were autoclaved together in the fermentors and serum bottles. Glucose, ammonium sulfate and potassium phosphate were all separately autoclaved. Ca-, Mg- and Na-chlorides were autoclaved together. After cooling down the fermentors and serum bottles the missing components were added as sterile stock solutions. For the seed cultures the same medium was used.

2. Cultivations and Analytics

The seed culture was grown anaerobically in a 100 mL-serum bottle with gas tight butyl rubber stoppers containing 50 mL medium at 39° C. in a shaking incubator (rotary speed: 160 rpm, shaking diameter: 2.5 cm). Inoculation of the seed culture was performed with 1 mL of the WCB (example 2) in the anaerobic chamber (MAKS MG 500, meintrup-dws). Immediately after the inoculation the gas atmosphere (80% $N_2$, 15% $CO_2$ and 5% $H_2$) was substituted by pure $CO_2$ with an overpressure of about 0.8 bar. After 9 h of incubation the fermentor was inoculated with 30 mL to start the cultivation in the fermentor (Sixfors, Infors Switzerland) containing 300 mL cultivation medium which had been gassed over night with $CO_2$ to ensure oxygen-free conditions. The cultivation temperature was maintained at 39° C. and the pH at 6.5 with 5 M NaOH. The $CO_2$-gas stream was adjusted to 0.25 vvm. The stirrer speed was adjusted to 500 rpm.

Glucose consumption and SA and by-product formation were measured by HPLC as described in example 1.

3. Results

Figure 10:
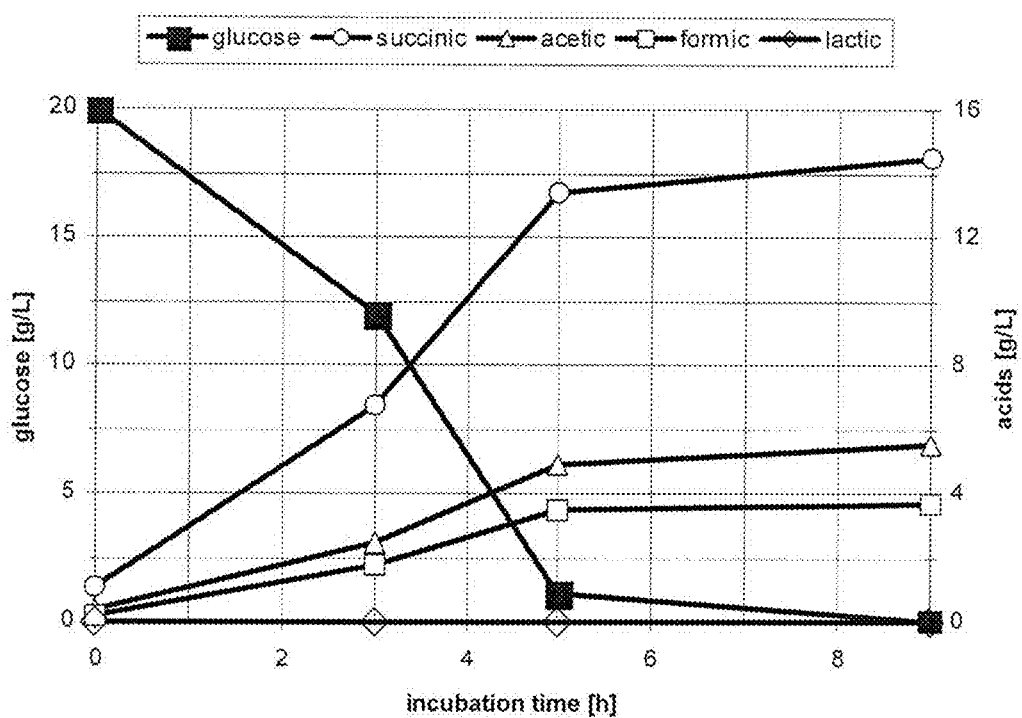
FIG. 10 shows the results of an anaerobic batch cultivation of DD1 under $CO_2$-saturation conditions with glucose as described by Lee et al., 2002a and 2002b.

The results are summarized in FIG. 10. Within 5 h of incubation 18.9 g/L of glucose are consumed and 12.3 g/L of succinic acid, 4.5 g/L of acetic acid and 3.3 g/L of formic acid are produced by DD1, indicating a product spectrum which is similar to the one of MBEL55E. However, the space time yield obtained with DD1 for succinic acid is 2.5 g/(L h), which is clearly higher than the one of strain MBEL55E (1.8 g/[L h], Lee et al., 2002b). The Yield is 0.7 g succinic acid/g glucose which is similar to the one of strain MBEL55E.

Example 13

Growth of DD1 in Synthetic Medium

It is favorable to use a synthetic medium without complex ingredients for the fermentation of DD1 in order to improve downstream processing and design a lean synthetic medium for cost efficient fermentation. Therefore, a synthetic medium was designed for DD1. Meanwhile, a synthetic medium had also been published for the close relative *Mannheimia succiniciproducens* (Song et al, 2008). Essential and stimulatory compounds had been determined for growth of DD1. Comparing the results with *Mannheimia succiniciproducens* obvious differences were observed, hinting to a more economic growth medium suitable for the strain DD1.

1. Medium Preparation

The synthetic growth medium for DD1 was developed in relation to other synthetic growth media for rumen bacteria (Nili and Brooker, 1995, McKinlay et al, 2005), previous in house experience with other bacteria and by performing single omission experiments. Finally, the medium contained 50 g/L glucose, 1 g/L $(NH_4)_2SO_4$, 0.2 g/L $CaCl_2*2H_2O$, 0.2 g/L $MgCl_2*6H_2O$, 1 g/L NaCl, 3 g/L $K_2HPO_4$, 1 mg/L nicotinic acid, 1.5 mg/L pantothenic acid, 5 mg/L pyridoxine, 5 mg/L riboflavin, 5 mg/L biotin, 1.5 mg/L thiamin HCl, 0.26 g/L lysine, 0.15 g/L threonine, 0.05 g/L methionine, 0.71 g/L glutamic acid, 0.06 g/L histidine, 0.07 g/L tryptophane, 0.13 g/L phenylalanine, 0.06 g/L tyrosine, 0.5 g/L serine, 0.5 g/L glycine, 0.5 g/L cysteine, 0.1 g/L β-Alanine, 0.27 g/L alanine, 0.19 g/L valine, 0.23 g/L leucine, 0.16 g/L isoleucine, 0.33 g/L aspartic acid, 0.1 g/L asparagine, 0.13 g/L proline, 0.15 g/L arginine and 0.1 g/L glutamine.

Serum bottles containing 50 mL of complex or synthetic medium were autoclaved with water and 30 g/L $MgCO_3$ as the buffer system. Glucose, ammonium sulfate and potassium phosphate were sterilized, separately. Ca-, Mg- and Na-chlorides were sterilized together. Vitamins and amino acids were assembled in various stock solutions and filter sterilized. After cooling down the serum bottles the components were added as sterile stock solutions.

Standard complex medium was prepared as described in example 12 without using polypeptone and starting at 50 g/L glucose and 30 g/L $MgCO_3$. For seed cultures and some main culture control experiments complex medium was used.

2. Cultivations and Analytics

The seed culture was grown in complex medium anaerobically using a 100 mL-serum bottle with gas tight butyl rubber stoppers containing 50 mL medium at 37° C. in a shaking incubator (rotary speed: 170 rpm, shaking diameter: 2.5 cm). Inoculation of the first seed culture was performed aerobically with 1 mL of the WCB (example 2) under sterile conditions. Immediately after inoculation the aerobic gas atmosphere was substituted by pure $CO_2$ with an overpressure of about 0.8 bar. After 8 h of incubation 2 ml of the first seed culture was centrifuged and washed three times using a sterile wash solution containing 2 g/L $(NH_4)_2SO_4$, 0.4 g/L $CaCl_2*2H_2O$, 0.4 g/L $MgCl_2*6H_2O$, 2 g/L NaCl and 6 g/L $K_2HPO_4$ before inoculation into the second seed culture 100 mL-serum bottle.

The incubation of the second seed culture occurred for 20 h as described for the first seed culture, before using 2 mL of the second culture again in order to inoculate the main culture, which was incubated for another 20 h. In order to determine essential or stimulatory compounds, the vitamin or amino acid of interest was omitted in the second seed culture and the main culture. Glucose consumption and Succinic acid formation were measured by HPLC as described in example 1.

3. Results

The results are summarized in table 16. It was observed that the medium omitting biotin and thiamin HCl did not sustain growth and succinic acid production. Biotin and thiamin HCl were therefore shown to be essential compounds for growth of DD1. Concentrations of biotin lower than 0.6 mg/L were sufficient for growth of DD1. The amino acid cysteine was found to be not essential for growth off DD1, as the omitting of cysteine lead to similar succinic acid production as in the cysteine containing control.

In contrast to these results, biotin was described as not essential but stimulatory and cysteine as essential for growth of *Mannheimia succiniciproducens* (Song et al, 2008). Thiamin HCl is essential for both organisms. A strain prototrophic for cysteine is expected to have a leaner and cheaper production medium for succinic acid production.

TABLE 16

Glucose consumption and succinic acid production by DD1 grown in synthetic medium

| Growth conditions | Glucose consumption [g/L] | Succinic Acid production [g/L] |
|---|---|---|
| Complete synthetic medium | 49.93 | 30.35 |
| Synthetic medium without biotin | 0.8 | 0.08 |
| Synthetic medium without thiamin HCl | 6.27 | 0.81 |
| Synthetic medium without cysteine | 48.88 | 30.01 |

Example 14

Metabolisation of Glycerol by the Strain DD1

The productivity of the strain DD1 in the presence of gylcerol as a carbon source was further analyzed utilizing the following optimized medium and incubation conditions:
1. Medium Preparation and Cultivation DD1 was grown in the following fashion. Cells from a frozen stock solution were streaked on an BHI-Agar plate (Becton Dickinson). Cells were scraped off and suspended in fresh BHI medium and incubated in an anaerobic serum bottle at 37° C. for 5.5 h. Cells were inoculated in the medium containing the compounds described in table 17 using 100 mL serum bottles. The start OD at 600 nm was 0.1 (determined in a 1 mL path). The medium components 1-7 were autoclaved together, compound 8 was autoclaved in the serum bottle, compounds 9 and 10 were autoclaved separately and added to the final medium. Serum bottles were sparged at least three times with $CO_2$ through butyl-rubber stoppers and left with a $CO_2$ overpressure of 0.8 bar. Serum bottles were incubated at 200 rpm and 37° C. After 24 h serum bottles were opened and metabolites were determined by HPLC as described in example 1.

TABLE 17

Medium composition

| | Compound | Concentration [g/L] |
|---|---|---|
| 1 | Bacto yeast extrakt (Becton Dickinson) | 5 |
| 2 | Polypeptone peptone (Becton Dickinson) | 10 |
| 3 | $(NH_4)_2SO_4$ | 2 |
| 4 | $CaCl_2*2H_2O$ | 0.2 |
| 5 | $MgCl_2*6H_2O$ | 0.2 |
| 6 | NaCl | 2 |
| 7 | $K_2HPO_4$ | 3 |
| 8 | $MgCO_3$ (Riedel-de Haen 13117) | 50 |
| 9 | $NaHCO_3$ | 25 |
| 10 | Glycerol | 70 |

TABLE 18

Results of example 14
Glycerol metabolisation

| $t_c$ [h]$^c$ | 24 |
|---|---|
| $\Delta c_{GI}$ [g/L]$^d$ | −28.4 |
| $\Delta c_{SA}$ [g/L]$^e$ | +35.3 |
| $\Delta c_{LA}$ [g/L]$^e$ | 0 |
| $\Delta c_{FA}$ [g/L]$^e$ | +2.4 |

TABLE 18-continued

Results of example 14
Glycerol metabolisation

| $\Delta c_{AA}$ [g/L]$^e$ | +2.5 |
|---|---|
| STY [g/(L h)]$^f$ | 1.47 |
| Yield [g/g]$^f$ | 1.24 |
| Ratio SA/FA$^g$ | 14.7 |
| Ratio SA/AA$^g$ | 14.1 |

$^c$cultivation time.
$^d$consumption of glycerol.
$^e$formation of succinic, lactic, formic and acetic acid.
$^f$space time yield and yield for succinic acid.
$^g$ratio g/L succinic acid per g side product formic acid (FA) and acetic acid (AA).

2. Results:

The following results were obtained as described in table 18. DD1 produced 35.3 g/L succinic acid from 28.4 g/L glycerol in 24 h, leading to a space time yield of 1.47 g/L succinic acid per h, which is superior to other documented examples of glycerol metabolisation (Lee et al. 2001). The yield of 1.24 g/g was close to the described theoretical yield of 1.29 g succinic acid per g of glycerol, if the turnover of 1M glycerol and 1M $CO_2$ to 1M succinic acid is achieved (Song and Lee, 2006).

Example 15

Production of Succinate Form Glycerol and Maltose

The productivity of DD1 in the presence of two carbon sources was determined. DD1 was grown in the presence of the disaccharide maltose and glycerol simultaneously.
1. Medium Preparation and Cultivation Cells from a frozen stock solution were streaked on a BHI-Agar plate (Becton Dickinson). Cells were scraped off and suspended in fresh BHI medium and incubated in an anaerobic serum bottle at 37° C. for 5.5 h. The medium is described in table 19. 200 mL serum bottles were used. Cells were inoculated with a start OD of 0.1 (determined in a 1 mL path with a pharmacia photometer at 600 nm). Serum bottles were sparged at least three times with $CO_2$ through butyl-rubber stoppers and left with a $CO_2$ overpressure of 0.8 bar. Serum bottles were incubated at 200 rpm and 37° C.

TABLE 19

Medium preparation for example 15

| Compound | Concentration [g/L] |
|---|---|
| Maltose * $H_2O$ | 22 |
| Glycerol | 56.82 |
| Bacto yeast extract | 10 |
| $(NH_4)_2SO_4$ | 2 |
| $CaCl_2*2H_2O$ | 0.2 |
| $MgCl_2*6H_2O$ | 0.2 |
| NaCl | 2 |
| $K_2HPO_4$ | 3 |
| $NaHCO_3$ | 8.4 |
| MgCO3 | 50 |
| Antifoam Polypropylenglycol 1200 | 0.1 |

The seed culture was inoculated with a 2 mL frozen culture grown anaerobically in a 200 mL serum bottle with gas tight butyl rubber stoppers containing 50 mL medium at 37° C. in a shaking incubator (rotary speed: 160 rpm, shaking diameter: 2.5 cm). The bottle was sparged by pure $CO_2$ with an overpressure of about 0.8 bar. After 8 h of incubation the fermentor was inoculated with 50 mL to start the cultivation in the fermentor containing 1 L cultivation medium which had been gassed with $CO_2$ to ensure oxygen-free conditions. The cultivation temperature was maintained at 37° C. and the pH at 6.5 without addition of bases except the buffer $MgCO_3$ in the medium. The $CO_2$-gas stream was adjusted to 0.2 vvm. The stirrer speed was adjusted to 300 rpm. Maltose and glycerol consumption and SA and by-product formation were measured by HPLC as described in example 1. Cells were grown at 37° C. and biomass was determined taking a sample and dissolving the residual $MgCO_3$ by the addition of 1M HCl. After dissolving $MgCO_3$ cells were washed with water and dried by lyophilization. Dry biomass was determined by weighing.

Results:

The results are summarized in table 20. Within 16 h of incubation 36.5 g/L of glycerol and 11.2 g/L maltose are consumed and 57.54 g/L of succinic acid, 3.41 g/L of acetic acid and 3.7 g/L of formic acid are formed by DD1. The space time yield obtained with DD1 for succinic acid is 3.4 g/(L h), which is clearly higher than previously reported for the strain MBEL55E and *Anaerobiospirillum succiniciproducens* and is superior to other strains described in literature (Lee et al, 2002b, Lee et al, 2001, Song and Lee, 2006).

The succinic acid yield was determined as 1.2 g succinic acid per g of carbon source for the sum of glycerol and maltose. This yield is also superior to strains described in literature (Lee et al, 2002b, Lee et al, 2001, Song and Lee, 2006).

The space time yield of 3.7 g/(L h) succinic acid is superior to strains described in literature (Song et al, 2006)

In addition the specific productivity for succinic acid of 0.77 [g gDCW$^{-1}$ h$^{-1}$]$^h$ was found to be superior to strains described in literature (Song et al, 2006).

TABLE 20

Results of example 15
Glycerol and maltose as carbon sources

| | |
|---|---|
| $t_c$ [h]$^b$ | 16 |
| Biomass BTM [g/L] | 4.7 |
| $\Delta c_{Glycerol}$[g/L]$^d$ | −36.5 |
| $\Delta c_{Succinic}$ acid[g/L]$^e$ | 57.54 |
| $\Delta C_{Maltose}$ [g/L]$^d$ | −11.2 |
| $\Delta c_{FA}$ [g/L]$^e$ | 3.7 |
| $\Delta c_{AA}$ [g/L]$^e$ | 3.41 |
| STY [g/(L h)]$^f$ | 3.4 |
| Yield succinate [g/g]$^g$ | 1.2 |
| Specific productivity for SA [g gDCW$^{-1}$ h$^{-1}$]$^h$ | 0.77 |

$^b$cultivation time
$^c$dry biomass as determined by solubilisation of $MgCO_3$.
$^d$consumption of glycerol or maltose
$^e$formation of succinic, formic and acetic acid
$^f$space time yield g succinic acid per (L *h)
$^g$yield g succinic acid per g substrate (sum of maltose and glycerol)
$^h$Specific productivity: g succinic acid per g biomass (dry cell weight) per h

SUMMARY OF THE EXPERIMENTS

1. Strain DD1 of the present invention has very promising features:
    Attractive productivity parameter's on glycerol (SA titer: up to 57 g/L, space time yield of 3.4 g/(L h) succinic acid, a specific productivity for succinic acid of 0.77 g/(g DCW h) and a carbon yield of up to 1.24 g/g carbon consumed.
    Glucose and glycerol levels of at least 75 g/L and 70 g/L respectively are tolerated.
    D-glucose, D-xylose, L-arabinose, D-galactose, D-mannose are efficiently converted into SA, indicating suitability for SA production with a biorefinery approach
    Glycerol, especially the unpurified material from bio diesel plants, is also efficiently used for SA production; Yields space time yields specific productivities and product/byproduct-ratios are substantially higher and better than with D-glucose and other sugars.
    $NH_3/NH_4OH$ for pH-control is tolerated, production of succinic acid and/or succinic acid ammonium salts is therefore possible
    D-glucose, D-xylose, L-arabinose, D-galactose, D-mannose are efficiently converted into SA, indicating suitability for SA production with a biorefinery approach
    Glycerol, especially the unpurified material from bio diesel plants, is also efficiently used for SA production; Yields and product/byproduct-ratios are substantially higher than with D-glucose and other sugars.
    The combination of separate carbon sources are efficiently converted into succinic acid
    Aerobic cell growth is possible, which is a clear advantage for the general handling of the strain in the lab, especially for further strain development
    The cultivation medium was substantially improved without productivity losses.

CONCLUSIONS

1. The strain has an excellent potential for the production of succinic acid and/or succinic acid salts, e.g. ammonium salts, which can be converted to THF/BDO/GBL and pyrrolidones.
2. Production of succinic acid for monomer applications is another attractive option.

REFERENCES

Dharmadi Y, Murarka A, Gonzalez R (2006) Anaerobic fermentation of glycerol by Escherichia coli: A new platform for metabolic engineering. Biotech Bioeng 94: 821-829.

Janssen P H (1991) Characterization of a succincate-fermenting anaerobic bacterium isolated from a glycolate-degrading mixed culture. Arch Microbiol 155: 288-293.

Jukes T H, Cantor C R (1969) Evolution of protein molecules. In: Mammalian Protein Metabolism, vol 3, pp 21-132. Edited by Munro H N. New York: Academic Press Kamm B, Kamm M, Schmidt M, Hirth T, Schulze M (2006) Lignocellulose-based chemical products and product family trees. In: Kamm B, Gruber, P R, Kamm M (eds.) Biorefineries—Industrial Processes and products. Status Quo and future directions. Vol. 2. Wiley-VCH, Weinheim.

Lee J (1997) Biological conversion of lignocellulosic biomass to ethanol. J Biotech 56: 1-24.

Lee P C, Lee S Y, Hong S A, Chang H N (2002a) Isolation and characterization of a new Succinic acid-producing bacterium, *Mannheimia succiniciproducens* MBEL 55E, from bovine rumen. Appl Microbiol Biotechnol 58: 663-668.

Lee P C, Lee W G, Lee S Y, Chang H N (2001) Succinic acid production with reduced by-product formation in the fermentation of *Anaerobiospirillum succiniciproducens* using glycerol as a carbon source. Biotech Bioeng 72: 41-48.

Lee S Y, Chang H N, Lee P C, Lee W G (2002b) Organic acid producing microorganism and process for preparing organic acids employing the same. WO 02/00846 A1.

Maidak B L, Cole J R, Parker Jr T C, Garrity G M, Larsen N, Li B, Lilburn T G, McCaughey M J, Olsen G J, Overbeek R, Pramanik S, Schmidt T M, Tiedje J M, Woese C R (1999) A new version of the RDP (Ribosomal Database Project). Nucl Acids Res 27:171-173.

McKinlay J, Zeikus J, Vieille C (2005) Insights into *Actinobacillus succinogenes* fermentative metabolism in a chemically defined growth medium. Appl Environ Microbiol 71: 6651-6656.

Nili N, Brooker J (1995) A defined medium for rumen bacteria and identification of strains impaired in de-novo biosynthesis of certain amino-acids. Lett Appl Microbiol 21: 69-74.

Peters-Wendisch, P G et al. ARCHIVES OF MICROBIOLOGY 165 387-396 1996.

Rainey F A, Ward-Rainey N, Kroppenstedt R M, Stackebrandt E (1996) The genus Nocardiopsis represents a phylogenetically coherent taxon and a distict actinomycete line-age: proposal of Nocardiopsaceae fam. nov. Int J Syst Bacteriol 46: 1088-1092.

Saitou N, Nei M (1987) The neighbor-joining method: a new method for reconstructing phylogenetic trees. Mol Biol Evol 4: 406-425.

Song H and Lee S (2006) Production of succinic acid by bacterial fermentation. Enz Microb Tech 39: 352-361.

Song H, Kim T, Choi B, Choi S, Nielsen L, Chang H, Lee S (2008) Development of chemically defined medium for *Mannheimia succiniciproducens* based on its genome sequence. Appl Microbiol Biotechnol 79: 263-272.

Yazdani S, Gonzalez R (2007) Anaerobic fermentation of glycerol: a path to economic viability for the biofuels industry. Curr Opinion Biotechnol 18: 213-219.

In the context of the present invention a bacterial strain DD1 was deposited with Deutsche Sammlung von Mikroorganismen and Zellkulturen GmbH (DSMZ, Inhoffenstr. 7B, D-38124 Braunschweig, Germany) on Aug. 11, 2006 having the deposit number DSM 18541. Access to this deposit will be available during the pendency of the application to the Commissioner of Patents and Trademarks and persons determined by the Commissioner to be entitled thereto upon request. Upon granting of any claims in the application, the Applicants will make the deposit available to the public pursuant to 37 CFR §1.808. The deposit will be maintained in the DSMZ Depository, which is a public depository, for a period of 30 years, or 5 years after the most recent request, or for the enforceable life of the patent, whichever is longer, and will be replaced if it becomes nonviable during that period. Applicants have no authority to waive any restrictions imposed by law on the transfer of biological material or its transportation in commerce. Applicants do not wave any infringement of their rights granted under this patent.

The invention claimed is:

1. A bacterial strain DD1 deposited in Deutsche Sammlung von Mikroorganismen and Zellkulturen GmbH (DSMZ) with deposition number DSM 18541 which has the ability to produce succinic acid and a variant or a mutant strain derived therefrom that retains the ability to produce succinic acid, wherein the strain and the variant or the mutant strain comprise 16S rDNA of SEQ ID NO: 1 or a nucleotide sequence having at least 99.9% sequence identity to SEQ ID NO: 1.

2. A process for the fermentative production of an organic acid or a salt thereof, which process comprises:
   a. incubating the bacterial strain of claim 1 in a medium containing an assimilable carbon source and cultivating said strain under conditions for the formation of the organic acid or salt thereof; and
   b. obtaining said organic acid or salt or derivative thereof from the medium.

3. The process of claim 2, wherein fermentation is performed at a temperature in the range of about 10 to 60° C. at a pH of 5.0 to 9.0 in the presence of carbon dioxide.

4. The process of claim 2, wherein said organic acid is succinic acid.

5. The process of claim 2, wherein the assimilable carbon source is selected from glycerol, sucrose, maltose, D-fructose, D-galactose, D-mannose, D-glucose, D-xylose, L-arabinose, decomposition products of starch, cellulose, hemicelluloses and lignocellulose; and mixtures thereof.

6. The process of claim 5, wherein the carbon source is glycerol or a mixture of glycerol and at least one further carbon source selected from sucrose, maltose, D-fructose, D-galactose, D-mannose, D-glucose, D-xylose, and L-arabinose.

7. The process of claim 2, wherein the concentration of the assimilable carbon source is adjusted to a value in a range of 5 to 80 g/l.

8. A process for the fermentative production of succinic acid or a salt thereof, which process comprises:
   a. incubating the bacterial strain of claim 1 in a medium containing at least one assimilable carbon source and cultivating said strain under conditions for the formation of the organic acid or salt thereof; and
   b. obtaining said organic acid or salt thereof from the medium;
   wherein the process additionally comprises at least one of the following:
   i. converting at least 28 g/L of glycerol to at least 28.1 g/L succinic acid, with a yield coefficient YP/S of at least 1.0 g/g;
   ii. converting at least one carbon source selected from sucrose, maltose, D-fructose, D-glucose, D-xylose, L-arabinose, D-galactose, D-mannose, or glycerol to succinic acid with a specific productivity yield of at least 0.6 g gDCW$^{-1}$ h$^{-1}$ succinic acid;

iii. converting at least one carbon source selected from sucrose, maltose, D-fructose, D-glucose, D-xylose, L-arabinose, D-galactose, D-mannose, or glycerol to succinic acid with a space time yield for succinic acid of at least 2.2 g/(L h) succinic acid;

iv. converting at least 28 g/L of at least one carbon source selected from sucrose, maltose, D-fructose, D-glucose, D-xylose, L-arabinose, D-galactose, D-mannose, or glycerol to succinic acid with a space-time-yield for succinic acid of at least 2.2 g/(L h);

v. converting at least one carbon source selected from sucrose, maltose, D-fructose, D-glucose, D-xylose, L-arabinose, D-galactose, D-mannose, or glycerol to succinic acid with a specific productivity yield of at least 0.6 g gDCW$^{-1}$ h$^{-1}$ succinic acid and a space-time-yield for succinic acid of at least 2.2 g/(L h).

9. The process of claim 2, performed discontinuously or continuously.

10. The process of claim 2, wherein succinic acid and/or salts thereof are obtained and wherein the process further comprises controlling the pH with ammonia or an aqueous solution thereof, or NH$_4$HCO$_3$, (NH$_4$)$_2$CO$_3$, NaOH, Na$_2$CO$_3$, NaHCO$_3$, KOH, K$_2$CO$_3$, KHCO$_3$, Mg(OH)$_2$, MgCO$_3$, MgH(CO$_3$)$_2$, Ca(OH)$_2$, CaCO$_3$, Ca(HCO$_3$)$_2$, CaO, CH$_6$N$_2$O$_2$, C$_2$H$_7$N and mixtures thereof.

11. The process of claim 10, further comprising
   a) direct catalytic hydrogenation of the obtained succinic acid and/or salts thereof to tetrahydrofuran (THF) and/or 1,4-butanediol (BDO) and/or gamma-butyrolactone (GBL); or
   b) chemical esterification of the obtained succinic acid and/or succinic acid salts to its corresponding di-lower-alkyl ester and subsequent catalytic hydrogenation of said ester to THF and/or BDO and/or GBL.

12. The process of claim 10, further comprising chemical conversion of succinic acid ammonium salts to pyrrolidones.

13. The process of claim 6, wherein said glycerol, which is used as assimilable carbon source, is obtained by ester cleavage of triacylglycerides.

14. The process of claim 13, wherein glycerol is a waste product as obtained from the manufacture of bio diesel.

15. The process of claim 2, wherein the assimilable carbon source is selected from glycerol, sucrose, glucose, and mixtures thereof.

16. The process of claim 10, wherein controlling the pH comprises using Mg(OH)$_2$.

* * * * *

SEQUENCE LISTING

```
<160> NUMBER OF SEQ ID NOS: 10

<210> SEQ ID NO 1
<211> LENGTH: 1517
<212> TYPE: DNA
<213> ORGANISM: Pasteurella sp.
<220> FEATURE:
<221> NAME/KEY: misc_feature
<222> LOCATION: (1)..(1517)
<223> OTHER INFORMATION: 16S rDNA

<400> SEQUENCE: 1
tttgatcctg gctcagattg aacgctggcg gcaggcttaa cacatgcaag tcgaacggta      60
gcgggaggaa agcttgcttt ctttgccgac gagtggcgga cgggtgagta atgcttgggg     120
atctggctta tggaggggga taacgacggg aaactgtcgc taataccgcg taatatcttc     180
ggattaaagg gtgggacttt cgggccaccc gccataagat gagcccaagt gggattaggt     240
agttggtggg gtaaaggcct accaagccga cgatctctag ctggtctgag aggatgacca     300
gccacactgg aactgagaca cggtccagac tcctacggga ggcagcagtg gggaatattg     360
cacaatgggg ggaaccctga tgcagccatg ccgcgtgaat gaagaaggcc ttcgggttgt     420
aaagttcttt cggtgacgag gaaggtgttt gttttaatag gacaagcaat tgacgttaat     480
cacagaagaa gcaccggcta actccgtgcc agcagccgcg gtaatacgga gggtgcgagc     540
gttaatcgga ataactgggc gtaaagggca tgcaggcgga ctttaagtg agatgtgaaa     600 gccccgggct taacctggga attgcatttc agactgggag tctagagtac tttagggagg     660
ggtagaattc cacgtgtagc ggtgaaatgc gtagagatgt ggaggaatac cgaaggcgaa     720
ggcagcccct tgggaagata ctgacgctca tatgcgaaag cgtgggagc aaacaggatt     780 agataccctg gtagtccacg cggtaaacgc tgtcgatttg gggattgggc tttaggcctg     840
gtgctcgtag ctaacgtgat aaatcgaccg cctggggagt acgccgcaa ggttaaaact     900 caaatgaatt gacggggggcc cgcacaagcg gtggagcatg tggtttaatt cgatgcaacg     960
```

```
cgaagaacct tacctactct tgacatccag agaatcctgt agagatacgg gagtgccttc   1020
gggagctctg agacaggtgc tgcatggctg tcgtcagctc gtgttgtgaa atgttgggtt   1080
aagtcccgca acgagcgcaa cccttatcct ttgttgccag catgtaaaga tgggaactca   1140
aaggagactg ccggtgacaa accggaggaa ggtggggatg acgtcaagtc atcatggccc   1200
ttacgagtag ggctacacac gtgctacaat ggtgcataca gagggcggcg ataccgcgag   1260
gtagagcgaa tctcagaaag tgcatcgtag tccggattgg agtctgcaac tcgactccat   1320
gaagtcggaa tcgctagtaa tcgcaaatca gaatgttgcg gtgaatacgt tcccgggcct   1380
tgtacacacc gcccgtcaca ccatgggagt gggttgtacc agaagtagat agcttaacct   1440
tcgggggggg cgtttaccac ggtatgattc atgactgggg tgaagtcgta caaggtaac    1500 cgtagggaa cctgcgg                                                   1517

<210> SEQ ID NO 2
<211> LENGTH: 3008
<212> TYPE: DNA
<213> ORGANISM: Pasteurella sp.
<220> FEATURE:
<221> NAME/KEY: misc_feature
<222> LOCATION: (1)..(3008)
<223> OTHER INFORMATION: 23S rDNA

<400> SEQUENCE: 2
agtaataacg aacgacacag gtataagaat acttgaggtt gtatggttaa gtgactaagc     60
gtacaaggtg gatgccttgg caatcagagg cgaagaagga cgtgctaatc tgcgaaaagc    120
ttgggtgagt tgataagaag cgtctaaccc aagatatccg aatggggcaa cccagtagat    180
gaagaatcta ctatcaataa ccgaatccat aggttattga ggcaaaccgg gagaactgaa    240
acatctaagt accccgagga aaagaaatca accgagatta cgtcagtagc ggcgagcgaa    300
agcgtaagag ccggcaagtg atagcatgag gattagagga atcggctggg aagccgggcg    360
gcacagggtg atagccccgt acttgaaaat cattgtgtgg tactgagctt gcgagaagta    420
gggcgggaca cgagaaatcc tgtttgaaga aggggggacc atcctccaag gctaaatact    480
cctgattgac cgatagtgaa ccagtactgt gaaggaaagg cgaaaagaac cccggtgagg    540
ggagtgaaat agaacctgaa accttgtacg tacaagcagt gggagcccgc gagggtgact    600
gcgtaccttt tgtataatgg gtcagcgact tatattatgt agcgaggtta accgaatagg    660
ggagccgaag ggaaaccgag tcttaactgg gcgtcgagtt gcatgatata gacccgaaac    720
ccggtgatct agccatgggc aggttgaagg ttgggtaaca ctaactggag gaccgaaccg    780
actaatgttg aaaaattagc ggatgacctg tggctggggg tgaaaggcca atcaaaccgg    840
gagatagctg gttctccccg aaatctattt aggtagagcc ttatgtgaat accttcgggg    900
gtagagcact gtttcggcta gggggccatc ccggcttacc aacccgatgc aaactgcgaa    960
taccgaagag taatgcatag gagacacacg gcgggtgcta acgttcgtcg tggagaggga   1020
aacaacccag accgccagct aaggtcccaa agtttatatt aagtgggaaa cgaagtggga   1080
aggcttagac agctaggatg ttggcttaga agcagccatc atttaaagaa agcgtaatag   1140
ctcactagtc gagtcggcct gcgcggaaga tgtaacgggg ctcaaatata gcaccgaagc   1200
tgcggcatca ggcgtaagcc tgttgggtag gggagcgtcg tgtaagcgga agaaggtggt   1260
tcgagagggc tgctggacgt atcacgagtg cgaatgctga cataagtaac gataaaacgg   1320
gtgaaaaacc cgttcgccgg aagaccaagg gttcctgtcc aacgttaatc ggggcagggt   1380
gagtcggccc ctaaggcgag gctgaagagc gtagtcgatg ggaaacgggt taatattccc   1440
```

```
gtacttgtta taattgcgat gtggggacgg agtaggttag gttatcgacc tgttggaaaa   1500
ggtcgtttaa gttggtaggt ggagcgttta ggcaaatccg gacgcttatc aacaccgaga   1560
gatgatgacg aggcgctaag gtgccgaagt aaccgatacc acacttccag gaaaagccac   1620
taagcgtcag attataataa accgtactat aaaccgacac aggtggtcag gtagagaata   1680
ctcaggcgct tgagagaact cgggtgaagg aactaggcaa aatagcaccg taacttcggg   1740
agaaggtgcg ccggcgtaga ttgtagaggt ataccettga aggttaaacc ggtcgaagtg   1800
acccgctggc tgcaactgtt tattaaaaac acagcactct gcaaacacga aagtggacgt   1860 ataggggtgtg atgcctgccc ggtgctggaa ggttaattga tggcgttatc gcaagagaag   1920
cgcctgatcg aagccccagt aaacggcggc cgtaactata acggtcctaa ggtagcgaaa   1980
ttccttgtcg ggtaagttcc gacctgcacg aatggcataa tgatggccag gctgtctcca   2040
cccgagactc agtgaaattg aaatcgccgt gaagatgcgg tgtacccgcg gctagacgga   2100 aagacccgt gaacctttac tatagcttga cactgaacct tgaattttga tgtgtaggat   2160
aggtgggagg ctttgaagcg gtaacgccag ttatcgtgga gccatccttg aaataccacc   2220
ctttaacgtt tgatgttcta acgaagtgcc cggaacgggt actcggacag tgtctggtgg   2280
gtagtttgac tggggcggtc tcctcccaaa gagtaacgga ggagcacgaa ggtttgctaa   2340
tgacggtcgg acatcgtcag gttagtgcaa tggtataagc aagcttaact gcgagacgga   2400
caagtcgagc aggtgcgaaa gcaggtcata gtgatccggt ggttctgaat ggaagggcca   2460
tcgctcaacg gataaaaggt actccgggga taacaggctg ataccgccca agagttcata   2520
tcgacggcgg tgtttggcac ctcgatgtcg gctcatcaca tcctggggct gaagtaggtc   2580
ccaagggtat ggctgttcgc catttaaagt ggtacgcgag ctgggtttaa aacgtcgtga   2640
gacagtttgg tccctatctg ccgtgggcgt tggagaattg agaggggctg ctcctagtac   2700
gagaggaccg gagtggacgc atcactggtg ttccggttgt gtcgccagac gcattgccgg   2760
gtagctacat gcggaagaga taagtgctga aagcatctaa gcacgaaact tgcctcgaga   2820
tgagttctcc cagtatttaa tactgtaagg gttgttggag acgacgacgt agataggccg   2880
ggtgtgtaag cgttgcgaga cgttgagcta accggtacta attgcccgag aggcttagcc   2940
atacaacgct caagtgtttt tggtagtgaa agttattacg gaataagtaa gtagtcaggg   3000
aatcggct                                                           3008
```

<210> SEQ ID NO 3
<211> LENGTH: 3024
<212> TYPE: DNA
<213> ORGANISM: Pasteurella sp.
<220> FEATURE:
<221> NAME/KEY: misc_feature
<222> LOCATION: (1)..(3024)
<223> OTHER INFORMATION: 23S rDNA 1

<400> SEQUENCE: 3

```
gttaagtgac taagcgtaca aggtggatgc cttggcaatc agaggcgaag aaggacgtgc     60
taatctgcga aaagcttggg tgagttgata agaagcgtct aacccaagat atccgaatgg    120
ggcaacccag tagatgaaga atctactatc aataaccgaa tccataggtt attgaggcaa    180
accgggagaa ctgaaacatc taagtacccc gaggaaaaga aatcaaccga gattacgtca    240
gtagcggcga gcgaaagcgt aagagccggg aagtgatagc atgaggatta gaggaaccgg    300
ctgggaagcc gggcggcaca gggtgatagc cccgtacttg aaaatcattg tgtggtactg    360
agcttgcgag aagtagggcg ggacacgaga aatcctgttt gaagaagggg ggaccatcct    420
```

```
ccaaggctaa atactcctga ttgaccgata gtgaaccagt actgtgaagg aaaggcgaaa      480
agaaccccgg tgaggggagt gaaatagaac ctgaaacctt gtacgtacaa gcagtgggag      540
cccgcgaggt tgactgcgta cctttttgtat aatgggtcag cgacttatat tatgtagcga     600
ggttaaccga atagggagc cgaagggaaa ccgagtctta actgggcgtc gagttgcatg       660
atatagaccc gaaacccggt gatctagcca tgggcaggtt gaaggttggg taacactaac      720
tggaggaccg aaccgactaa tgttgaaaaa ttagcggatg acctgtggct ggggggtgaaa    780 ggccaatcaa accgggagat agctggttct ccccgaaatc tatttaggta gagccttatg     840 tgaataccttt cggggtaga gcactgtttc ggctaggggg ccatcccggc ttaccaaccc     900
gatgcaaact gcgaataccg aagagtaatg cataggagac acacggcggg tgctaacgtt     960
cgtcgtggag agggaaacaa cccagaccgc cagctaaggt cccaaagttt atattaagtg    1020
ggaaacgaag tgggaaggct tagacagcta ggatgttggc ttagaagcag ccatcattta    1080
aagaaagcgt aatagctcac tagtcgagtc ggcctgcgcg gaagatgtaa cggggctcaa    1140
atatagcacc gaagctgcgg catcaggcgt atcactaata cgccttacga ttaacaactt    1200
gcgaaggaag agagcaagtt ggttaagcga ccaacacgtt gagtcggctg taagcgagag    1260
cgaacagaaa ggcgcgagtg gagcgtgagg aatattagtg atacgcctgt gggtaggggg    1320
agcgtcgtgt aagcggaaga aggtggttcg agagggctgc tggacgtatc acgagtgcga    1380
atgctgacat aagtaacgat aaaacggggtg aaaaacccgt tcgccggaag accaagggtt   1440
cctgtccaac gttaatcggg gcaggggtgag tcggccccta aggcgaggct gaagagcgta   1500
gtcgatggga aacgggttaa tattcccgta cttgttataa ttgcgatgtg gggacggagt   1560
aggttaggtt atcgacctgt tggaaatggt cgtttaagtt ggtaggtgga gcgtttaggc    1620
aaatccggac gcttatcaac accgagagat gatgacgagg cgctaaggtg ccgaagtaac   1680
cgataccaca cttccaggaa aagccactaa gcgtcagatt ataataaacc gtactataaa    1740
ccgacacagg tggtcaggta gagaatactc aggcgcttga gagaactcgg gtgaaggaac    1800
taggcaaaat agcaccgtaa cttcgggaga aggtgcgccg cgtagattg tagaggtata     1860 cccttgaagg ttgaaccggt cgaagatacc agctggctgc aactgtttat taaaaacaca    1920
gcactctgca aacacgaaag tggacgtata gggtgtgatg cctgcccggt gctgaaggt    1980 taattgatgg cgttatcgca agagaagcgc ctgatcgaag cccagtaaa cggcggccgt     2040 aactataacg gtcctaaggt agcgaaattc cttgtcgggt aagttccgac ctgcacgaat    2100
ggcataatga tggccaggct gtctccaccc gagactcagt gaaattgaaa tcgccgtgaa    2160
gatgcggtgt acccgcggct agacggaaag accccgtgaa cctttactat agcttgacac   2220
tgaaccttga attttgatgt gtaggatagg tgggaggctt gaagcggta acgccagtta     2280 tcgtggagcc atccttgaaa taccacccctt taacgtttga tgttctaacg aagtgcctgg   2340
aacgggtact cggacagtgt ctggtgggta gtttgactgg ggcggtctcc tcccaaagag    2400
taacggagga gcacgaaggt ttgctaatga cggtcggaca tcgtcaggtt agtgcaatgg    2460
tataagcaag cttaactgcg agacggacaa gtcgagcagg tgcgaaagca ggtcatagtg    2520
atccggtggt tctgaatgga agggccatcg ctcaacggat aaaaggtact ccggggataa    2580
caggctgata ccgcccaaga gttcatatcg acggcggtgt ttggcacctc gatgtcggct    2640
catcacatcc tggggctgaa gtaggtccca agggtatggc tgttcgccat ttaaagtggt    2700
acgcgagctg ggtttaaaac gtcgtgagac agtttggtcc ctatctgccg tgggcgttgg    2760
agaattgaga ggggctgctc ctagtacgag aggaccggag tggacgcatc actggtgttc    2820
```

| | |
|---|---|
| cggttgtgtc gccagacgca ttgccgggta gctacatgcg aagagataa gtgctgaaag | 2880 |
| catctaagca cgaaacttgc ctcgagatga gttctcccag tatttaatac tgtaagggtt | 2940 |
| gttggagacg acgacgtaga taggccgggt gtgtaagcgt tgcgagacgt tgagctaacc | 3000 |
| ggtactaatt gcccgagagg ctta | 3024 |

<210> SEQ ID NO 4
<211> LENGTH: 3023
<212> TYPE: DNA
<213> ORGANISM: Pasteurella sp.
<220> FEATURE:
<221> NAME/KEY: misc_feature
<222> LOCATION: (1)..(3023)
<223> OTHER INFORMATION: 23S rDNA 2

<400> SEQUENCE: 4

| | |
|---|---|
| gttaagtgat taagcgtaca aggtggatgc cttggcaatc agaggcgaag aaggacgtgc | 60 |
| taatctgcga aaagcttggg tgagttgata agaagcgtct aacccaagat atccgaatgg | 120 |
| ggcaacccag tagatgaaga atctactatc aataaccgaa tccataggtt attgaggcaa | 180 |
| accgggagaa ctgaaacatc taagtacccc gaggaaaaga atcaaccga gattacgtca | 240 |
| gtagcggcga gcgaaagcgt aagagccggc aagtgatagc atgaggatta gaggaaccgg | 300 |
| ctgggaagcc gggcggcaca gggtgatagc cccgtacttg aaaatcattg tgtggtactg | 360 |
| agcttgcgag aagtagggcg ggacacgaga atcctgtttt gaagaagggg ggaccatcct | 420 |
| ccaaggctaa atactcctga ttgaccgata gtgaaccagt actgtgaagg aaaggcgaaa | 480 |
| agaaccccgg tgaggggagt gaaatagaac ctgaaaccct gtacgtacaa gcagtgggag | 540 |
| cccgcgaggg tgactgcgta ccttttgtat aatgggtcag cgacttatat tatgtagcga | 600 |
| ggttaaccga ataggggagc cgaagggaaa ccgagtctta actgggcgtc gagttgcatg | 660 |
| atatagaccc gaaacccggt gatctagcca tgggcaggtt gaaggttggg taacactaac | 720 |
| tggaggaccg aaccgactaa tgttgaaaaa ttagcggatg acctgtggct gggggtgaaa | 780 |
| ggccaatcaa accgggagat agctggttct ccccgaaatc tatttaggta gagccttatg | 840 |
| tgaataccct cggggggtaga gcactgtttc ggctaggggg ccatcccggc ttaccaaccc | 900 |
| gatgcaaact gcgaataccg aagagtaatg cataggagac acggcggg tgctaacgtt | 960 |
| cgtcgtggag agggaaacaa cccagaccgc cagctaaggt cccaaagttt atattaagtg | 1020 |
| ggaaacgaag tgggaaggct tagacagcta ggatgttggc ttagaagcag ccatcattta | 1080 |
| aagaaagcgt aatagctcac tagtcgagtc ggcctgcgcg gaagatgtaa cggggctcaa | 1140 |
| atatagcacc gaagctgcgg catcaggcgt atcactaata cgccttacga ttaacaactt | 1200 |
| gcgaaggaag agagcaagtt ggttaagcga ccaacacgtt gagtcggctg taagcgagag | 1260 |
| cgaacagaaa ggcgcgagtg gagcgtgagg aatattagtg atacgcctgt tgggtagggg | 1320 |
| agcgtcgtgt aagcggaaga aggtggtgtg gggacggagt aggttaggtt atcgacctgt | 1380 |
| tggaaatggt cgtttaagtt ggtaggtgga gcgtttaggc aaatccggac gcttatcaac | 1440 |
| accgagcaac gttaatcggg gcagggtgag tcggccccta aggcgaggct gaagagcgta | 1500 |
| gtcgatggga aacgggttaa tattcccgta cttgttataa ttgcgattcg agagggctgc | 1560 |
| tggacgtatc acgagtgcga atgctgacat aagtaacgat aaaacgggtg aaaaaccgt | 1620 |
| tcgccggaag accagggttc ctgtcagatg atgacgaggc ctaaggtgc cgaagtaacc | 1680 |
| gataccacac ttccaggaaa agccactaag cgtcagatta taataaaccg tactataaac | 1740 |
| cgacacaggt ggtcaggtag agaatactca ggcgcttgag agaactcggg tgaaggaact | 1800 |

```
aggcaaaata gcaccgtaac ttcgggagaa ggtgcgccgg cgtagattgt agaggtatac    1860
ccttgaaggt tgaaccggtc gaagatacca gctggctgca actgtttatt aaaaacacag    1920
cactctgcaa acacgaaagt ggacgtatag ggtgtgatgc ctgcccggtg ctggaaggtt    1980
aattgatggc gttatcgcaa gagaagcgcc tgatcgaagc cccagtaaac ggcggccgta    2040
actataacgg tcctaaggta gcgaaattcc ttgtcgggta agttccgacc tgcacgaatg    2100
gcataatgat ggccaggctg tctccacccg agactcagtg aaattgaaat cgccgtgaag    2160
atgcggtgta cccgcggcta gacggaaaga ccccgtgaac ctttactata gcttgacact    2220
gaaccttgaa ttttgatgtg taggataggt gggaggcttt gaagcggtaa cgccagttat    2280
cgtggagcca tccttgaaat accacccttt aacgtttgat gttctaacga agtgcctgga    2340
acgggtactc ggacagtgtc tggtgggtag tttgactggg gcggtctcct cccaaagagt    2400
aacggaggag cacgaaggtt tgctaatgac ggtcggacat cgtcaggtta gtgcaatggt    2460
ataagcaagc ttaactgcga gacggacaag tcgagcaggg gcgaaagcag gtcatagtga    2520
tccggtggtt ctgaatggaa gggccatcgc tcaacggata aaaggtactc cggggataac    2580
aggctgatac cgcccaagag ttcatatcga cggcggtgtt tggcacctcg atgtcggctc    2640
atcacatcct ggggctgaag taggtcccaa gggtatggct gttcgccatt taaagtggta    2700
cgcgagctgg gtttaaaacg tcgtgagaca gtttggtccc tatctgccgt gggcgttgga    2760
gaattgagag gggctgctcc tagtacgaga ggaccggagt ggacgcatca ctggtgttcc    2820
ggttgtgtcg ccagacgcat tgccgggtag ctacatgcgg aagagataag tgctgaaagc    2880
atctaagcac gaaacttgcc tcgagatgag ttctcccagt atttaatact gtaagggttg    2940
ttggagacga cgacgtagat aggccgggtg tgtaagcgtt gcgagacgtt gagctaaccg    3000
gtactaattg cccgagaggc tta                                            3023

<210> SEQ ID NO 5
<211> LENGTH: 3023
<212> TYPE: DNA
<213> ORGANISM: Pasteurella sp.
<220> FEATURE:
<221> NAME/KEY: misc_feature
<222> LOCATION: (1)..(3023)
<223> OTHER INFORMATION: 23S rDNA 3

<400> SEQUENCE: 5
gttaagtgac taagcgtaca aggtggatgc cttggcaatc agaggcgaag aaggacgtgc      60
taatctgcga aaagcttggg tgagttgata agaagcgtct aacccaagat atccgaatgg     120
ggcaacccag tagatgaaga atctactatc aataaccgaa tccataggtt attgaggcaa     180
accgggagaa ctgaaacatc taagtacccc gaggaaaaga aatcaaccga gattacgtca     240
gtagcggcga gcgaaagcgt aagagccggc aagtgatagc atgaggatta gaggaaccgg     300
ctgggaagcc gggcggcaca gggtgatagc cccgtacttg aaaatcattg tgtggtactg     360
agcttgcgag aagtagggcg ggacacgaga atcctgtttt gaagaagggg ggaccatcct     420
ccaaggctaa atactcctga ttgaccgata gtgaaccagt actgtgaagg aaaggcgaaa     480
agaaccccgg tgaggggagt gaaatagaac ctgaaacctt gtacgtacaa gcagtgggag     540
cccgcgaggg tgactgcgta ccttttgtat aatgggtcag cgacttatat tatgtagcga     600
ggttaaccga atagggggagc cgaagggaaa ccgagtctta actgggcgtc gagttgcatg     660
atatagaccc gaaaccccggt gatctagcca tgggcaggtt gaaggttggg taacactaac     720
tggaggaccg aaccgactaa tgttgaaaaa ttagcggatg acctgtggct gggggtgaaa     780
```

```
ggccaatcaa accgggagat agctggttct ccccgaaatc tatttaggta gagccttatg    840
tgaatacctt cggggtaga gcactgtttc ggctaggggg ccatcccggc ttaccaaccc     900
gatgcaaact gcgaataccg aagagtaatg cataggagac acacggcggg tgctaacgtt    960
cgtcgtggag agggaaacaa cccagaccgc acgctaaggt cccaaagttt atattaagtg   1020
ggaaacgaag tgggaaggct tagacagcta ggatgttggc ttagaagcag ccatcattta   1080
aagaaagcgt aatagctcac tagtcgagtc ggcctgcgcg gaagatgtaa cggggctcaa   1140
atatagcacc gaagctgcgg catcaggcgt atcactaata cgccttacga ttaacaactt   1200
gcgaaggaag agagcaagtt ggttaagcga ccaacacgtt gagtcggctg taagcgagag   1260
cgaacagaaa ggcgcgagtg gagcgtgagg aatattagtg atacgcctgt tgggtagggg   1320
agcgtcgtgt aagcggaaga aggtggttcg agagggctgc tggacgtatc acgagtgcga   1380
atgctgacat aagtaacgat aaaacggggtg aaaaacccgt tcgccggaag accagggttc   1440
ctgtccaacg ttaatcgggg cagggtgagt cggcccctaa ggcgaggctg aagagcgtag   1500
tcgatgggaa acgggttaat attcccgtac ttgttataat tgcgatgtgg ggacggagta   1560
ggttaggtta tcgacctgtt ggaaatggtc gtttaagttg gtaggtggag cgtttaggca   1620
aatccggacg cttatcaaca ccgagagatg atgacgaggc gctaaggtgc cgaagtaacc   1680
gataccacac ttccaggaaa agccactaag cgtcagatta taataaaccg tactataaac   1740
cgacacaggt ggtcaggtag agaatactca ggcgcttgag agaactcggg tgaaggaact   1800
aggcaaaata gcaccgtaac ttcgggagaa ggtgcgccgg cgtagattgt agaggtatac   1860
ccttgaaggt tgaaccggtc gaagatacca gctggctgca actgtttatt aaaaacacag   1920
cactctgcaa acacgaaagt ggacgtatag ggtgtgatgc ctgcccggtg ctggaaggtt   1980
aattgatggc gttatcgcaa gagaagcgcc tgatcgaagc cccagtaaac ggcggccgta   2040
actataacgg tcctaaggta gcgaaattcc ttgtcgggta agttccgacc tgcacgaatg   2100
gcataatgat ggccaggctg tctccacccg agactcagtg aaattgaaat cgccgtgaag   2160
atgcggtgta cccgcggcta gacggaaaga ccccgtgaac ctttactata gcttgacact   2220
gaaccttgaa ttttgatgtg taggataggt gggaggcttt gaagcggtaa cgccagttat   2280
cgtggagcca tccttgaaat accaccctt aacgtttgat gttctaacga agtgcctgga   2340
acgggtactc ggacagtgtc tggtgggtag tttgactggg gcggtctcct cccaaagagt   2400
aacgaggag cacgaaggtt tgctaatgac ggtcggacat cgtcaggtta gtgcaatggt   2460
ataagcaagc ttaactgcga gacggacaag tcgagcaggt gcgaaagcag gtcatagtga   2520
tccggtggtt ctgaatggaa gggccatcgc tcaacggata aaaggtactc cggggataac   2580
aggctgatac cgcccaagag ttcatatcga cggcggtgtt tggcacctcg atgtcggctc   2640
atcacatcct ggggctgaag taggtcccaa gggtatggct gttcgccatt taaagtggta   2700
cgcgagctgg gtttaaaacg tcgtgagaca gtttggtccc tatctgccgt gggcgttgga   2760
gaattgagag gggctgctcc tagtacgaga ggaccggagt ggacgcatca ctggtgttcc   2820
ggttgtgtcg ccagacgcat tgccgggtag ctacatgcgg aagagataag tgctgaaagc   2880
atctaagcac gaaacttgcc tcgagatgag ttctcccagt atttaatact gtaagggttg   2940
ttggagacga cgacgtagat aggccgggtg tgtaagcgtt gcgagacgtt gagctaaccg   3000
gtactaattg cccgagaggc tta                                           3023
```

<210> SEQ ID NO 6
<211> LENGTH: 3024

<212> TYPE: DNA
<213> ORGANISM: Pasteurella sp.
<220> FEATURE:
<221> NAME/KEY: misc_feature
<222> LOCATION: (1)..(3024)
<223> OTHER INFORMATION: 23S rDNA 4

<400> SEQUENCE: 6

```
gttaagtgac taagcgtaca aggtggatgc cttggcaatc agaggcgaag aaggacgtgc      60
taatctgcga aaagcttggg tgagttgata agaagcgtct aacccaagat atccgaatgg     120
ggcaacccag tagatgaaga atctactatc aataaccgaa tccataggtt attgaggcaa     180
accgggagaa ctgaaacatc taagtacccc gaggaaaaga aatcaaccga gattacgtca     240
gtagcggcga gcgaaagcgt aagagccggc aagtgatagc atgaggatta gaggaaccgg     300
ctgggaagcc gggcggcaca gggtgatagc cccgtacttg aaaatcattg tgtggtactg     360
agcttgcgag aagtagggcg ggacacgaga atcctgtttt gaagaagggg ggaccatcct     420
ccaaggctaa atactcctga ttgaccgata gtgaaccagt actgtgaagg aaaggcgaaa     480
agaaccccgg tgagggagt gaaatagaac ctgaaacctt gtacgtacaa gcagtgggag     540
cccgcgaggg tgactgcgta cctttgtat aatgggtcag cgacttatat tatgtagcga     600
ggttaaccga atagggggagc cgaagggaaa ccgagtctta actgggcgtc gagttgcatg     660
atatagaccc gaaacccggt gatctagcca tgggcaggtt gaaggttggg taacactaac     720
tggaggaccg aaccgactaa tgttgaaaaa ttagcggatg acctgtggct gggggtgaaa     780
ggccaatcaa accgggagat agctggttct ccccgaaatc tatttaggta gagccttatg     840
tgaataccct cggggggtaga gcactgtttc ggctaggggg ccatcccggc ttaccaaccc     900
gatgcaaact gcgaataccg aagagtaatg cataggagac acggcgggg tgctaacgtt     960
cgtcgtggag agggaaacaa cccagaccgc cagctaaggt cccaaagttt atattaagtg    1020
ggaaacgaag tgggaaggct tagacagcta ggatgttggc ttagaagcag ccatcattta    1080
aagaaagcgt aatagctcac tagtcgagtc ggcctgcgcg gaagatgtaa cggggctcaa    1140
atatagcacc gaagctgcgg catcaggcgt atcactaata cgccttacga ttaacaactt    1200
gcgaaggaag agagcaagtt ggttaagcga ccaacacgtt gagtcggctg taagcgagag    1260
cgaacagaaa ggcgcgagtg gagcgtgagg aatattagtg atacgcctgt tgggtaggggg    1320
agcgtcgtgt aagcggaaga aggtggttcg agagggctgc tggacgtatc acgagtgcga    1380
atgctgacat aagtaacgat aaaacgggtg aaaaacccgt tcgccggaag accaaggggtt    1440
cctgtccaac gttaatcggg gcagggtgag tcggcccccta aggcgaggct gaagagcgta    1500
gtcgatggga acgggttaa tattcccgta cttgttataa ttgcgatgtg gggacgggagt    1560
aggttaggtt atcgacctgt tggaaatggt cgtttaagtt ggtaggtgga gcgtttaggc    1620
aaatccggac gcttatcaac accgagagat gatgacgagg cgctaaggtg ccgaagtaac    1680
cgataccaca cttccaggaa aagccactaa gcgtcagatt ataataaacc gtactataaa    1740
ccgacacagg tggtcaggta gagaatactc aggcgcttga gagaactcgg gtgaaggaac    1800
taggcaaaat agcaccgtaa cttcgggaga aggtgcgccg gcgtagattg tagaggtata    1860
cccttgaagg ttgaaccggt cgaagatacc agctggctgc aactgtttat taaaaacaca    1920
gcactctgca aacacgaaag tggacgtata gggtgtgatg cctgcccggt gctggaaggt    1980
taattgatgg cgttatcgca agagaagcgc ctgatcgaag ccccagtaaa cggcggccgt    2040
aactataacg gtcctaaggt agcgaaattc cttgtcgggt aagttccgac ctgcacgaat    2100
ggcataatga tggccaggct gtctccaccc gagactcagt gaaattgaaa tcgccgtgaa    2160
```

```
gatgcggtgt acccgcggct agacggaaag accccgtgaa cctttactat agcttgacac    2220
tgaaccttga attttgatgt gtaggatagg tgggaggctt tgaagcggta acgccagtta    2280
tcgtggagcc atccttgaaa taccacccett taacgtttga tgttctaacg aagtgcctgg    2340
aacgggtact cggacagtgt ctggtgggta gtttgactgg ggcggtctcc tcccaaagag    2400
taacggagga gcacgaaggt tgctaatga cggtcggaca tcgtcaggtt agtgcaatgg    2460
tataagcaag cttaactgcg agacggacaa gtcgagcagg tgcgaaagca ggtcatagtg    2520
atccggtggt tctgaatgga agggccatcg ctcaacggat aaaaggtact ccggggataa    2580
caggctgata ccgcccaaga gttcatatcg acggcgtgt ttggcacctc gatgtcggct    2640
catcacatcc tggggctgaa gtaggtccca agggtatggc tgttcgccat ttaaagtggt    2700
acgcgagctg ggtttaaaac gtcgtgagac agtttggtcc ctatctgccg tgggcgttgg    2760
agaattgaga ggggctgctc ctagtacgag aggaccggag tggacgcatc actggtgttc    2820
cggttgtgtc gccagacgca ttgccgggta gctacatgcg gaagagataa gtgctgaaag    2880
catctaagca cgaaacttgc ctcgagatga gttctcccag tatttaatac tgtaagggtt    2940
gttggagacg acgacgtaga taggccgggt gtgtaagcgt tgcgagacgt tgagctaacc    3000
ggtactaatt gcccgagagg ctta                                          3024

<210> SEQ ID NO 7
<211> LENGTH: 3024
<212> TYPE: DNA
<213> ORGANISM: Pasteurella sp.
<220> FEATURE:
<221> NAME/KEY: misc_feature
<222> LOCATION: (1)..(3024)
<223> OTHER INFORMATION: 23S rDNA 5

<400> SEQUENCE: 7
gttaagtgac taagcgtaca aggtggatgc cttggcaatc agaggcgaag aaggacgtgc      60
taatctgcga aaagcttggg tgagttgata agaagcgtct aacccaagat atccgaatgg     120
ggcaacccag tagatgaaga atctactatc aataaccgaa tccataggtt attgaggcaa     180
accgggagaa ctgaaacatc taagtacccc gaggaaaaga aatcaaccga gattacgtca     240
gtagcggcga gcgaaagcgt aagagccggc aagtgatagc atgaggatta gaggaaccgg     300
ctgggaagcc gggcggcaca gggtgatagc cccgtacttg aaaatcattg tgtggtactg     360
agcttgcgag aagtagggcg ggacacgaga atcctgtttt gaagaagggg ggaccatcct     420
ccaaggctaa atactcctga ttgaccgata gtgaaccagt actgtgaagg aaaggcgaaa     480
agaaccccgg tgaggggagt gaaatagaac ctgaaacctt gtacgtacaa gcagtgggag     540
cccgcgaggg tgactgcgta cctttttgtat aatgggtcag cgacttatat tatgtagcga     600
ggttaaccga ataggggagc cgaagggaaa ccgagtctta actgggcgtc gagttgcatg     660
atatagaccc gaaacccggt gatctagcca tgggcaggtt gaaggttggg taacactaac     720
tggaggaccg aaccgactaa tgttgaaaaa ttagcggatg acctgtggct ggggtgaaa     780 ggccaatcaa accgggagat agctggttct ccccgaaatc tatttaggta gagccttatg     840 tgaataccett cggggtaga gcactgtttc ggctaggggg ccatcccggc ttaccaaccc      900
gatgcaaact gcgaataccg aagagtaatg cataggagac acgcgcggg tgctaacgtt      960 cgtcgtggag agggaaacaa cccagaccgc cagctaaggt cccaaagttt atattaagtg    1020
ggaaacgaag tgggaaggct tagacagcta ggatgttggc ttagaagcag ccatcattta    1080
aagaaagcgt aatagctcac tagtcgagtc ggcctgcgcg gaagatgtaa cggggctcaa    1140
```

```
atatagcacc gaagctgcgg catcaggcgt atcactaata cgccttacga ttaacaactt   1200
gcgaaggaag agagcaagtt ggttaagcga ccaacacgtt gagtcggctg taagcgagag   1260
cgaacagaaa ggcgcgagtg gagcgtgagg aatattagtg atacgcctgt tgggtagggg   1320
agcgtcgtgt aagcggaaga aggtggttcg agagggctgc tggacgtatc acgagtgcga   1380
atgctgacat aagtaacgat aaaacgggtg aaaaacccgt tcgccggaag accaagggtt   1440
cctgtccaac gttaatcggg gcagggtgag tcggcccta aggcgaggct gaagagcgta    1500
gtcgatggga aacgggttaa tattcccgta cttgttataa ttgcgatgtg gggacggagt   1560
aggttaggtt atcgacctgt tggaaatggt cgtttaagtt ggtaggtgga gcgtttaggc   1620
aaatccggac gcttatcaac accgagagat gatgacgagg cgctaaggtg ccgaagtaac   1680
cgatgccacg cttccaggaa aagccactaa gcgtcagatt ataataaacc gtactataaa   1740
ccgacacagg tggtcaggta gagaatactc aggcgcttga gagaactcgg gtgaaggaac   1800
taggcaaaat agcaccgtaa cttcgggaga aggtgcgccg gcgtagattg tagaggtata   1860
cccttgaagg ttgaaccggt cgaagatacc agctggctgc aactgtttat taaaaacaca   1920
gcactctgca aacacgaaag tggacgtata gggtgtgatg cctgcccggt gctggaaggt   1980
taattgatgg cgttatcgca agagaagcgc ctgatcgaag ccccagtaaa cggcggccgt   2040
aactataacg gtcctaaggt agcgaaattc cttgtcgggt aagttccgac ctgcacgaat   2100
ggcataatga tggccaggct gtctccaccc gagactcagt gaaattgaaa tcgccgtgaa   2160
gatgcggtgt acccgcggct agacggaaag acccccgtgaa cctttactat agcttgacac   2220
tgaaccttga attttgatgt gtaggatagg tgggaggctt tgaagcggta acgccagtta   2280
tcgtggagcc atccttgaaa taccacccct taacgtttga tgttctaacg aagtgcctgg   2340
aacgggtact cggacagtgt ctggtgggta gtttgactgg ggcggtctcc tcccaaagag   2400
taacggagga gcacgaaggt ttgctaatga cggtcggaca tcgtcaggtt agtgcaatgg   2460
tataagcaag cttaactgcg agacggacaa gtcgagcagg tgcgaaagca ggtcatagtg   2520
atccggtggt tctgaatgga agggccatcg ctcaacggat aaaaggtact ccggggataa   2580
caggctgata ccgcccaaga gttcatatcg acggcggtgt ttggcacctc gatgtcggct   2640
catcacatcc tggggctgaa gtaggtccca agggtatggc tgttcgccat ttaaagtggt   2700
acgcgagctg ggtttaaaac gtcgtgagac agtttggtcc ctatctgccg tgggcgttgg   2760
agaattgaga ggggctgctc ctagtacgag aggaccggag tggacgcatc actggtgttc   2820
cggttgtgtc gccagacgca ttgccgggta gctacatgcg gaagagataa gtgctgaaag   2880
catctaagca cgaaacttgc ctcgagatga gttctcccag tatttaatac tgtaagggtt   2940
gttggagacg acgacgtaga taggccgggt gtgtaagcgt tgcgagacgt tgagctaacc   3000
ggtactaatt gcccgagagg ctta                                         3024
```

<210> SEQ ID NO 8
<211> LENGTH: 3024
<212> TYPE: DNA
<213> ORGANISM: Pasteurella sp.
<220> FEATURE:
<221> NAME/KEY: misc_feature
<222> LOCATION: (1)..(3024)
<223> OTHER INFORMATION: 23S rDNA 6

<400> SEQUENCE: 8

```
gttaagtgat taagcgtaca aggtggatgc cttggcaatc agaggcgaag aaggacgtgc     60
taatctgcga aaagcttggg tgagttgata agaagcgtct aacccaagat atccgaatgg    120
```

```
ggcaacccag tagatgaaga atctactatc aataaccgaa tccataggtt attgaggcaa      180
accgggagaa ctgaaacatc taagtacccc gaggaaaaga aatcaaccga gattacgtca      240
gtagcggcga gcgaaagcgt aagagccggc aagtgatagc atgaggatta gaggaaccgg      300
ctgggaagcc gggcggcaca gggtgatagc cccgtacttg aaaatcattg tgtggtactg      360
agcttgcgag aagtagggcg ggacacgaga atcctgtttt gaagaagggg ggaccatcct      420
ccaaggctaa atactcctga ttgaccgata gtgaaccagt actgtgaagg aaaggcgaaa      480
agaaccccgg tgaggggagt gaaatagaac ctgaaacctt gtacgtacaa gcagtgggag      540
cccgcgaggg tgactgcgta ccttttgtat aatgggtcag cgacttatat tatgtagcga      600
ggttaaccga atagggggagc cgaagggaaa ccgagtctta actgggcgtc gagttgcatg      660
atatagaccc gaaacccggt gatctagcca tgggcaggtt gaaggttggg taacactaac      720
tggaggaccg aaccgactaa tgttgaaaaa ttagcggatg acctgtggct gggggtgaaa      780
ggccaatcaa accgggagat agctggttct ccccgaaatc tatttaggta gagccttatg      840
tgaatacctt cggggtaga gcactgtttc ggctaggggg ccatcccggc ttaccaaccc      900
gatgcaaact gcgaataccg aagagtaatg cataggagac acgggcgggg tgctaacgtt      960
cgtcgtggag agggaaacaa cccagaccgc cagctaaggt cccaaagttt atattaagtg     1020
ggaaacgaag tgggaaggct tagacagcta ggatgttggc ttagaagcag ccatcattta     1080
aagaaagcgt aatagctcac tagtcgagtc ggcctgcgcg aagatgtaa cggggctcaa     1140 atatagcacc gaagctgcgg catcaggcgt atcactaata cgccttacga ttaacaactt     1200
gcgaaggaag agagcaagtt ggttaagcga ccaacacgtt gagtcggctg taagcgagag     1260
cgaacagaaa ggcgcgagtg gagcgtgagg aatattagtg atacgcctgt tgggtagggg     1320
agcgtcgtgt aagcggaaga aggtggttcg agagggctgc tggacgtatc acgagtgcga     1380
atgctgacat aagtaacgat aaaacggggtg aaaaacccgt tcgccggaag accaagggtt     1440
cctgtccaac gttaatcggg gcagggtgag tcggccccta aggcgaggct gaagagcgta     1500
gtcgatggga aacgggttaa tattcccgta cttgttataa ttgcgatgtg gggacggagt     1560
aggttaggtt atcgacctgt tggaaatggt cgtttaagtt ggtaggtgga gcgtttaggc     1620
aaatccggac gcttatcaac accgagagat gatgacgagg cgctaaggtg ccgaagtaac     1680
cgataccaca cttccaggaa aagccactaa gcgtcagatt ataataaacc gtactataaa     1740
ccgacacagg tggtcaggta gagaatactc aggcgcttga gagaactcgg gtgaaggaac     1800
taggcaaaat agcaccgtaa cttcgggaga aggtgcgccg gcgtagattg tagaggtata     1860
cccttgaagg ttgaaccggt cgaagatacc agctggctgc aactgtttat taaaaacaca     1920
gcactctgca aacacgaaag tggacgtata gggtgtgatg cctgcccggt gctggaaggt     1980
taattgatgg cgttatcgca agagaagcgc ctgatcgaag ccccagtaaa cggcggccgt     2040
aactataacg gtcctaaggt agcgaaattc cttgtcgggt aagttccgac ctgcacgaat     2100
ggcataatga tggccaggct gtctccaccc gagactcagt gaaattgaaa tcgccgtgaa     2160
gatgcggtgt acccgcggct agacggaaag accccgtgaa cctttactat agcttgacac     2220
tgaaccttga ttttgatgt gtaggatagg tgggaggctt tgaagcggta acgccagtta     2280
tcgtggagcc atccttgaaa taccacccctt taacgtttga tgttctaacg aagtgcctgg     2340
aacgggtact cggacagtgt ctggtgggta gtttgactgg gcggtctcc tcccaaagag     2400 taacggagga gcacgaaggt ttgctaatga cggtcggaca tcgtcaggtt agtgcaatgg     2460
tataagcaag cttaactgcg agacggacaa gtcgagcagg tgcgaaagca ggtcatagtg     2520
```

```
atccggtggt tctgaatgga agggccatcg ctcaacggat aaaaggtact ccggggataa      2580
caggctgata ccgcccaaga gttcatatcg acggcggtgt ttggcacctc gatgtcggct      2640
catcacatcc tggggctgaa gtaggtccca agggtatggc tgttcgccat ttaaagtggt      2700
acgcgagctg ggtttaaaac gtcgtgagac agtttggtcc ctatctgccg tgggcgttgg      2760
agaattgaga ggggctgctc ctagtacgag aggaccggag tggacgcatc actggtgttc      2820
cggttgtgtc gccagacgca ttgccgggta gctacatgcg aagagataa  gtgctgaaag      2880 catctaagca cgaaacttgc ctcgagatga gttctcccag tatttaatac tgtaagggtt      2940
gttggagacg acgacgtaga taggccgggt gtgtaagcgt tgcgagacgt tgagctaacc      3000
ggtactaatt gcccgagagg ctta                                             3024

<210> SEQ ID NO 9
<211> LENGTH: 20
<212> TYPE: DNA
<213> ORGANISM: Pasteurella sp.
<220> FEATURE:
<221> NAME/KEY: misc_feature
<222> LOCATION: (1)..(20)
<223> OTHER INFORMATION: PCR_primers: forward primer

<400> SEQUENCE: 9
agtaataacg aacgacacag                                                    20

<210> SEQ ID NO 10
<211> LENGTH: 18
<212> TYPE: DNA
<213> ORGANISM: Pasteurella sp.
<220> FEATURE:
<221> NAME/KEY: misc_feature
<222> LOCATION: (1)..(18)
<223> OTHER INFORMATION: PCR_primers: reverse primer

<400> SEQUENCE: 10
agccgattcc ctgactac                                                      18
```